US011185523B2

(12) United States Patent
Gainer

(10) Patent No.: US 11,185,523 B2
(45) Date of Patent: Nov. 30, 2021

(54) USE OF BIPOLAR TRANS CAROTENOIDS WITH CHEMOTHERAPY AND RADIOTHERAPY FOR TREATMENT OF CANCER

(71) Applicant: DIFFUSION PHARMACEUTICALS LLC, Charlottesville, VA (US)

(72) Inventor: John L. Gainer, Charlottesville, VA (US)

(73) Assignee: DIFFUSION PHARMACEUTICALS LLC, Charlottesville, VA (US)

( * ) Notice: Subject to any disclaimer, the term of this patent is extended or adjusted under 35 U.S.C. 154(b) by 0 days.

(21) Appl. No.: 16/087,993

(22) PCT Filed: Mar. 23, 2017

(86) PCT No.: PCT/US2017/023844
§ 371 (c)(1),
(2) Date: Sep. 24, 2018

(87) PCT Pub. No.: WO2017/165667
PCT Pub. Date: Sep. 28, 2017

(65) Prior Publication Data
US 2019/0083439 A1    Mar. 21, 2019

Related U.S. Application Data

(60) Provisional application No. 62/312,988, filed on Mar. 24, 2016.

(51) Int. Cl.
*A61K 31/202* (2006.01)
*A61K 31/337* (2006.01)
(Continued)

(52) U.S. Cl.
CPC .......... *A61K 31/202* (2013.01); *A61K 9/0019* (2013.01); *A61K 9/19* (2013.01);
(Continued)

(58) Field of Classification Search
CPC .................................................. A61K 31/202
(Continued)

(56) References Cited

U.S. PATENT DOCUMENTS

| 2,175,843 A | 10/1939 | Kuhn et al. |
| 2,948,748 A | 8/1960 | Guex et al. |

(Continued)

FOREIGN PATENT DOCUMENTS

| AU | 2003215396 | 9/2003 |
| CA | 2477245 | 9/2003 |

(Continued)

OTHER PUBLICATIONS

Iannaccone et al., Dis Model Meeh. May-Jun. 2009; 2(5-6): 206-210. (Year: 2009).*

(Continued)

*Primary Examiner* — Deborah D Carr
(74) *Attorney, Agent, or Firm* — Hoxie & Associates LLC

(57) ABSTRACT

The subject disclosure relates to compounds and compositions including chemotherapy agents and/or radiation therapy with bipolar trans carotenoids, and the use of such compounds for the treatment of various cancers including pancreatic and brain cancers.

33 Claims, 4 Drawing Sheets

(51) Int. Cl.
*A61K 31/7068* (2006.01)
*A61K 47/40* (2006.01)
*A61K 9/19* (2006.01)
*A61K 31/704* (2006.01)
*A61K 45/06* (2006.01)
*A61K 31/495* (2006.01)
*A61K 9/00* (2006.01)
*A61K 33/243* (2019.01)
*A61K 47/64* (2017.01)
*A61P 35/00* (2006.01)
*A61K 31/4188* (2006.01)
*A61N 5/10* (2006.01)

(52) U.S. Cl.
CPC ........ *A61K 31/337* (2013.01); *A61K 31/4188* (2013.01); *A61K 31/495* (2013.01); *A61K 31/704* (2013.01); *A61K 31/7068* (2013.01); *A61K 33/243* (2019.01); *A61K 45/06* (2013.01); *A61K 47/40* (2013.01); *A61K 47/643* (2017.08); *A61N 5/1077* (2013.01); *A61P 35/00* (2018.01); *A61N 2005/1098* (2013.01)

(58) Field of Classification Search
USPC ........................................................ 514/649
See application file for complete search history.

(56) References Cited

U.S. PATENT DOCUMENTS

| | | | |
|---|---|---|---|
| 3,489,806 A | 1/1970 | Gutmann et al. |
| 3,687,990 A | 8/1972 | Gutmann et al. |
| 3,788,468 A | 1/1974 | Gainer |
| 3,853,933 A | 12/1974 | Siciliano |
| 3,853,993 A | 12/1974 | Gainer |
| 3,965,261 A | 6/1976 | Gainer |
| 3,975,519 A | 8/1976 | Gainer |
| 4,009,270 A | 2/1977 | Gainer, Jr. |
| 4,038,144 A | 7/1977 | Gainer |
| 4,046,880 A | 9/1977 | Gainer |
| 4,070,460 A | 1/1978 | Gainer, Jr. |
| 4,099,270 A | 7/1978 | Jabour |
| 4,105,855 A | 8/1978 | Schulz et al. |
| 4,176,179 A | 11/1979 | Gainer |
| 4,216,211 A | 8/1980 | Francis |
| 4,699,664 A | 10/1987 | Hettiarachchy et al. |
| 4,727,064 A | 2/1988 | Pitha |
| 5,032,613 A | 7/1991 | Watson |
| 5,053,240 A | 10/1991 | Todd, Jr. |
| 5,107,030 A | 4/1992 | Babler |
| 5,424,407 A | 6/1995 | Tanaka et al. |
| 5,472,946 A | 12/1995 | Peck et al. |
| 5,811,119 A | 9/1998 | Mehta et al. |
| 5,817,332 A | 10/1998 | Urtti et al. |
| 6,060,511 A | 5/2000 | Gainer |
| 6,150,561 A | 11/2000 | Kreienbuhl et al. |
| 6,235,311 B1 | 5/2001 | Ullah et al. |
| 6,555,526 B2 | 4/2003 | Matsuo et al. |
| 6,855,734 B2 | 2/2005 | Messadek |
| 7,145,025 B2 | 12/2006 | Lockwood et al. |
| 7,317,008 B2 | 1/2008 | Lockwood et al. |
| 7,351,844 B2 | 4/2008 | Gainer et al. |
| 7,446,101 B1 | 11/2008 | Madhavi et al. |
| 7,521,584 B2 | 4/2009 | Lockwood et al. |
| 7,759,506 B2 | 7/2010 | Gainer et al. |
| 7,887,840 B2 | 2/2011 | Curatolo et al. |
| 7,919,527 B2 | 4/2011 | Gainer et al. |
| 8,017,653 B2 | 9/2011 | Gainer et al. |
| 8,030,350 B2 | 10/2011 | Gainer et al. |
| 8,206,751 B2 | 6/2012 | Gainer |
| 8,269,027 B2 | 9/2012 | Gainer et al. |
| 8,293,804 B2 | 10/2012 | Gainer |
| 8,901,174 B2 | 12/2014 | Gainer |
| 8,974,822 B2 | 3/2015 | Gainer et al. |
| 9,604,899 B2 | 3/2017 | Gainer et al. |
| 9,950,067 B2 | 4/2018 | Gainer et al. |
| 10,016,384 B2 | 7/2018 | Gainer et al. |
| 10,130,689 B2 | 11/2018 | Gainer |
| 2003/0180281 A1 | 9/2003 | Bott et al. |
| 2003/0180282 A1 | 9/2003 | Serebruany et al. |
| 2003/0186931 A1 | 10/2003 | Matsuo et al. |
| 2004/0109920 A1 | 6/2004 | Reuscher et al. |
| 2004/0162329 A1 | 8/2004 | Lockwood et al. |
| 2006/0194973 A1* | 8/2006 | Gainer ................ A61K 31/202 554/121 |
| 2006/0233877 A1 | 10/2006 | Messadek et al. |
| 2006/0276372 A1 | 12/2006 | Lockwood et al. |
| 2006/0281724 A1 | 12/2006 | Loria |
| 2007/0088248 A1 | 4/2007 | Glenn |
| 2007/0135521 A1 | 6/2007 | Okada et al. |
| 2007/0161610 A1 | 7/2007 | Gainer et al. |
| 2007/0166339 A1 | 7/2007 | Gupta |
| 2008/0113031 A1 | 5/2008 | Moodley et al. |
| 2009/0110746 A1* | 4/2009 | Gainer ................... A61P 19/02 424/601 |
| 2009/0118227 A1 | 5/2009 | Jouni et al. |
| 2009/0169586 A1 | 7/2009 | Tracton |
| 2009/0176287 A1 | 7/2009 | Schmidt-Dannert et al. |
| 2010/0322918 A1 | 12/2010 | Gainer |
| 2011/0196038 A1 | 8/2011 | Gainer et al. |
| 2011/0300213 A1 | 12/2011 | Gainer et al. |
| 2012/0095099 A1 | 4/2012 | Gainer et al. |
| 2013/0018014 A1 | 1/2013 | Gainer |
| 2014/0051759 A1 | 2/2014 | Gainer et al. |
| 2017/0202798 A1 | 7/2017 | Gainer et al. |
| 2018/0271979 A1 | 9/2018 | Gainer et al. |
| 2019/0038586 A1 | 2/2019 | Gainer et al. |
| 2019/0083584 A1 | 3/2019 | Gainer |

FOREIGN PATENT DOCUMENTS

| | | |
|---|---|---|
| CA | 2524573 A1 | 11/2004 |
| CH | 522 572 | 10/1969 |
| CN | 1215723 | 5/1999 |
| CN | 1671643 | 9/2005 |
| CN | 1708480 | 12/2005 |
| CN | 1243120 | 2/2006 |
| CN | 1842512 | 10/2006 |
| CN | 1997365 | 7/2007 |
| CN | 10-1180257 | 5/2008 |
| CN | 100033 | 11/2016 |
| EP | 0 612 815 | 8/1994 |
| EP | 0 908 449 | 9/1998 |
| EP | 1 192 947 | 4/2002 |
| EP | 1 621 199 A1 | 2/2006 |
| EP | 1 667 954 | 6/2006 |
| GB | 2 353 934 | 3/2001 |
| JP | 45-014114 | 5/1970 |
| JP | 63-059831 | 3/1983 |
| JP | 61-254161 | 11/1986 |
| JP | 63-222114 | 9/1988 |
| JP | 1-238536 | 9/1989 |
| JP | 02-121934 | 5/1990 |
| JP | A 03-056412 | 3/1991 |
| JP | A 04-264020 | 9/1992 |
| JP | 05-032531 | 2/1993 |
| JP | A 05-178765 | 7/1993 |
| JP | 06-248193 | 9/1994 |
| JP | 07-023736 | 1/1995 |
| JP | 07-223960 | 8/1995 |
| JP | A 07-291854 | 11/1995 |
| JP | 09-512552 | 12/1997 |
| JP | 10-502388 | 3/1998 |
| JP | 11-19261 | 1/1999 |
| JP | 11-029466 | 2/1999 |
| JP | A--11-80901 | 7/1999 |
| JP | 11-209642 | 8/1999 |
| JP | 2000-007570 | 1/2000 |
| JP | 2001-511135 | 8/2001 |
| JP | 2001-302517 | 10/2001 |
| JP | 2002-524535 | 8/2002 |
| JP | 2002-538113 | 11/2002 |

(56) References Cited

FOREIGN PATENT DOCUMENTS

| | | |
|---|---|---|
| JP | 2003-026607 | 1/2003 |
| JP | 2003-201238 | 7/2003 |
| JP | 2005-053841 | 3/2005 |
| JP | 2005-518453 | 6/2005 |
| JP | 2006-525270 | 11/2006 |
| JP | 2006-342108 | 12/2006 |
| JP | 2007-522076 | 8/2007 |
| JP | 2010-106029 | 12/2009 |
| JP | 2010-090151 | 4/2010 |
| JP | 2010-229137 | 5/2010 |
| KR | 1999-0036861 | 5/1999 |
| KR | 10-2006-0020616 | 3/2006 |
| KR | 10-2010-0016396 | 2/2010 |
| RU | 2107496 | 3/1998 |
| RU | 2226096 | 3/2004 |
| RU | 2256446 | 7/2005 |
| RU | 2265434 | 12/2005 |
| WO | WO 1992/015544 | 9/1992 |
| WO | WO 1995/000130 | 1/1995 |
| WO | WO 1998/014183 | 4/1998 |
| WO | WO 1998/032421 | 7/1998 |
| WO | WO 1999/015150 | 4/1999 |
| WO | WO 2000/015262 | 3/2000 |
| WO | WO 2001/013933 A2 | 3/2001 |
| WO | WO 2001/013933 A3 | 9/2002 |
| WO | WO 2003/059270 A2 | 7/2003 |
| WO | WO 2003/072734 | 9/2003 |
| WO | WO 2004/005353 | 1/2004 |
| WO | WO 2004/011423 | 2/2004 |
| WO | WO 2004/041284 A1 | 5/2004 |
| WO | WO 2004/048323 | 6/2004 |
| WO | WO 2004/049095 | 6/2004 |
| WO | WO 2004/091630 A1 | 10/2004 |
| WO | WO 2004/049095 A3 | 12/2004 |
| WO | WO 2005/004854 | 1/2005 |
| WO | WO 2005/028411 | 3/2005 |
| WO | WO 2005/120495 | 12/2005 |
| WO | WO 2006/039685 | 4/2006 |
| WO | WO 2006/083780 A2 | 8/2006 |
| WO | WO 2006/093348 | 9/2006 |
| WO | WO 2006/104610 | 10/2006 |
| WO | WO 2007/072529 | 6/2007 |
| WO | WO 2008/014685 | 2/2008 |
| WO | WO 2008/027687 | 3/2008 |
| WO | WO 2008/102563 | 8/2008 |
| WO | WO 2008/135090 | 11/2008 |
| WO | WO 2008/136900 | 11/2008 |
| WO | WO 2009/058399 | 5/2009 |
| WO | WO 2009/111688 | 9/2009 |
| WO | WO 2010/151314 | 12/2010 |
| WO | WO 2011/152869 | 12/2011 |
| WO | WO 2017/165667 | 9/2017 |

OTHER PUBLICATIONS

Badyal et al., Indian J Pharmacol. May-Jun. 2014; 46(3): 257-265. (Year: 2014).*
Nebendahl, Procedures, "Routes of Administration", pp. 463-482, 2000. (Year: 2000).*
"Rat | Understanding Animal Research | Understanding Animal Research", http://www.understandinganimalresearch.org.uk/animals/10-facts/rat (Year: 2020).*
Sheehan, J. et al., "Trans-sodium Crocetinate Enhancing Survival and Glioma Response on Magnetic Resonance Imaging to Radiation and Temozolomide: Laboratory Investigation," J Neurosurg., vol. 113, pp. 234-239. (Year: 2010).*
Sheehan, J. et al., "Use of Trans Sodium Crocetinate for Sensitizing Glioblastoma Multiforme to Radiation," J Neurosurg., vol. 108, pp. 972-978. (Year: 2008).*
U.S. Appl. No. 60/907,718, filed Apr. 13, 2007, Gainer, J.L.
U.S. Appl. No. 61/001,095, filed Oct. 31, 2007, Gainer, J.L., et al.
U.S. Appl. No. 61/350,804, filed Jun. 2, 2010, Gainer, J.L., et al.
U.S. Appl. No. 16/030,496, filed Jul. 9, 2018, Gainer, J.L., et al.
U.S. Appl. No. 16/193,762, filed Nov. 16, 2018, Gainer, J.L.
Ahmad, A.S. et al., "Neuroprotection by cretin in a hemi-parkinsonian rat model," *Pharmacology Biochemistry and Behavior*, vol. 81, pp. 805-813, (2005).
Abusuev, A.A., "Clinical Course of Myocardial Infarction in Treatment with Perfluorane, in Perfluorocarbon Compounds in Experimental and Clinical Medicine," *Collected Works of the Russian Scientific Conference*, St. Petersburg, 2004, p. 12 (No English Translation Available.).
Bennett, M.H. et al., "Hyperbaric oxygen therapy for late radiation tissue injury (Review)," *The Cochrane Collaboration* Published by John Wiley & Sons, Ltd., Copyright 2009, Issue 2.
Boileau, T. W.-M., et al., "Bioavailability of all-trans and cis-Isomers of Lycopene," *Experimental Biology and Medicine*, vol. 227, pp. 914-919, (2002); http://ebm.sagepub.com/content/227/10/914.
Borisova, I.V. et al., "Renal and Neuroprotective Effects of Perfluorane in Induced Toxic Renal Injury in Rats," Medline.ru-Biomeditsinskii Zhurnal, vol. 5, Art. 16, pp. 136-139, (2004).
Britton, G. et al., "Isolation and Analysis," *Carotenoids*, vol. IA, pp. 103-107; p. 283, Birkhauser Verlag, Basel, (1995).
Broderick, J.P., et al., "Finding the Most Powerful Measures of the Effectiveness of Tissue Plasminogen Activator in the NINDS tPA Stroke Trial," *Stroke*, vol. 31, No. 10, pp. 2335-2341, (2000).
Brown, J. Martin, et al., "The Unique Physiology of Solid Tumors: Opportunities (and Problems) for Cancer Therapy," *Cancer Research*, vol. 58, pp. 1408-1416, (1998).
Buchta and Andree, "The Total Synthesis of trans-2,2-Bisdimethyl-crocetin-dimetyl ester and trans-Crocetin-dimethyl ester," *Naturwiss*, (1959).
Buchta, E. et al, "Eine Totalsynthese des „all-trans-Crocetin-dimethylesters2", *Chemischte Berichte Jahrg.*, vol. 93, pp. 1349-1353, (1960).
Bui, Q-C et al., "The Efficacy of Hyperbaric Oxygen Therapy in the Treatment of Radiation-Induced Late Side Effects, " *Int. J. Radiation Oncology Biol. Phys.*, vol. 60, No. 3, pp. 871-878, (2004).
Burukhina, A.N. et al., "Experience of Using Perfluorane in Treating Acute Massive Hemorrhage in Obstetric Practice, in Collected Works of the 12th Scientific and Practical Conference of Physicians Topical Issues in Modern Medicine," *Novosibirsk*, Chapter 2, pp. 39-40, (2002).
Calvo, W. et al., "Time- and dose-related changes in the white matter of the rat brain after single doses of X rays," *The British Journal of Radiology*, vol. 61, pp. 1043-1052, (1988).
Cianci, P. "Hyperbaric therapy for radiation injury," *Radiation Injury, Advances in Management and Prevention* edited by J.L. Meyer, et al., pp. 98-109, (1999).
Cheng, N.T. et al., "Intravenous thrombolysis for acute ischemic stroke within 3 hours versus between 3 and 4.5 hours of symptom onset," *The Neurohospitalist*, vol. 5, Issue 3, pp. 101-109; (2015).
Clark, W.M., et al., "The rtPA (Alteplase) 0-to 6-Hour Acute Stroke Trial, Part A (A0276g): Results of a Double-Blind, Placebo-Controlled, Multicenter Study," *Stroke*, vol. 31, No. 4, pp. 311-816, (2000).
CMC Co. Ltd., published Pharmaceutical Formulation Strategies and New Technology, Mar. 31, 2007, first printing, p. 88.
Coppola, G.M., "Amberlyst-15, A Superior Acid Catalyst for the Cleavage of Actetals," *Syn. Communications* 1021 (1984).
Craw, M. and Lambert, C., "The Characterisation of the Triplet State of Crocetin, a Water Soluble Carotenoid, by Nanosecond Laser Flash Photolyses," *Photochemistry and Photobiology*, vol. 38, No. 2, pp. 241-243, (1983).
Chryssanthi, D.G., et al., "A New Validated SPE-HPLC Method for Monitoring Crocetin in Human Plasma—Application After Saffron Tea Consumption," Journal of Pharmaceutical and Biomedical Analysis, vol. 55, pp. 563-568, (2011); DOI: 10.1016/j.jpba.2011.02.018.
Cutright, D.E. et al., "Long-Term Effects of Radiation on the Vascularity of Rat Bone—Quantitative Measurements with a New Technique," Radiation Research, vol. 48, pp. 402-408 (1971).
Database Caplus, Chemical Abstracts Service, Columbus, Ohio, US, (1988), XP002317165 [JP 63 059831].

(56) References Cited

OTHER PUBLICATIONS

Database Caplus, Chemical Abstracts Service, Columbus, Ohio, US, (1993), XP002317166 [JP 05 032531].
Denninghoff, et al., "Retinal Imaging Techniques in Diabetes," *Diabetes Technology & Therapeutics*, vol. 2, No. 1, pp. 111-113 (2000).
Finney, J., et al., "Protection of the ischemic heart with DMSO alone or DMSO with hydrogen peroxide," *Annals of the New York Academy of Sciences*, vol. 141, No. I, pp. 231-241, (1967).
Gainer, J.L., et al., "Oxygen diffusion and atherosclerosis," *Atherosclerosis*, vol. 19, pp. 135-138, (1974).
Gainer, J.L. et al., "Using Excess Volume of Mixing to Correlate Diffusivities in Liquids," *Chem. Eng. Commun.*, vol. 15, pp. 323-329, (1982).
Gainer, J.L., et al., "The Effect of Crocetin on Hemorrhagic Shock in Rats," *Circulatory Shock*, vol. 41, pp. 1-7, (1993).
Gainer, J.L., "Altering Diffusivities in Dilute Polymeric and Biological Solutions," *Ind. Engr. Chem. Research*, vol. 33, pp. 2341-2344, (1994).
Gainer, J.L. et al., "The effect of trans sodium crocetinate (TSC) in a rat oleic acid model of acute lung injury," *Pulmonary Pharmacology & Therapeutics*, Academic Press, GB, vol. 18, No. 3, pp. 213-216, (2005), XP004737366.
Gainer, J. L., "Trans-Sodium Crocetinate for Treating Hypoxia/Ischemia," *Expert Opinion on Investigational Drugs*, vol. 17, No. 6, pp. 917-924, (2008).
Galinski, Erwin A., et al., "The Kosmotropic (Structure-Forming) Effect of Compensatory Solutes," *Comp. Biochem. Physiol.*, vol. 117A, No. 3, pp. 357-365, (1997).
General Information on Perfluorane, Medline.ru-Biomeditsinskii Zhumal, vol. 5, Art. 16, pp. 68-69, (2004), www.medline.ru/public/art/tom5/art8-perf2.phtm (with English translation).
Ghandehari, K. et al., "Thrombolysis in stroke patients; Problems and limitations," *Iran Journal of Med. Sci.*, vol. 35, Issue 2, pp. 145-148, (2010).
Giassi, L.J. et al., "Trans Sodium Crocetinate Restores Blood Pressure, Heart Rate, and Plasma Lactate after Hemorrhagic Shock," *Journal of Trauma*, vol. 51, pp. 932-938, (2001).
Giassi, L.J., et al., "Trans Sodium Crocetinate for Hemorrhagic Shock: Effect of Time Delay in Initiating Therapy," *Shock*, vol. 18, No. 6, pp. 585-588, (2002).
Gibson, T.W. et al., "Sulfinic Acid Catalyzed Isomerization of Olefins," *J. Org. Chem.*, vol. 41, No. 5, pp. 791-793 (1976), XP002325593.
Gill, A.L. et al., "Hyperbaric oxygen: its uses, mechanisms of action and outcomes," *Q. J. Med.*, vol. 97, pp. 385-395, (2004).
Goldstick, T.K., Ph.D, "Diffusion of Oxygen in Protein Solutions," Dissertation, University of California, Berkeley, CA, pp. 13-28, (1966).
Gree, R. et al., "Fumaraldehyde Monodimethyl Acetal: An Easily Accessible and Versatile Intermediate," *Tetrahedron Letters*, vol. 27, No. 41, pp. 4983-4986, (1986).
Greenwood, T.W. et al., "Hyperbaric Oxygen and Wound Healing in Post-Irradiation Head and Neck Surgery," Brit. J. Surg., vol. 60, No. 5, pp. 394-397, (1973).
Group, N.r.-P.S.S., "Tissue Plasminogen Activator for Acute Ischemic Stroke," *The New England Journal of Medicine*, vol. 333, No. 24, pp. 1581-1587, (1995).
Holland, R.A.B. et al., "Kinetics of O2 Uptake and Release by Red Cells in Stopped-Flow Apparatus: Effects of unstirred Layer," *Respiration Physiology*, vol. 59, pp. 71-91, (1985).
Holloway, G.M., et al., "The carotenoid crocetin enhances pulmonary oxygenation," *The American Physiological Society*, pp. 683-686, Department of Chemical Engineering, and Dept. of Anesthesiology, School of Medicine, Univ. of VA, Charlotteville, Va, (1988).
Huxley, V.H., et al., "The Effect of the Red Cell Membrane and a Diffusion Boundary Layer on the Rate of Oxygen Uptake by Human Erythrocytes," *J. Physiol.*, vol. 316, pp. 75-83, (1981).

International Preliminary Examination Report on Patentability (IPRP) (Chapter 1) for PCT/US2003/005521, prepared Aug. 23, 2004.
International Preliminary Report on Patentability dated May 25, 2007 in PCT/US2003/026424; prepared May 10, 2007.
International Preliminary Report on Patentability for International Application No. PCT/US2006/006422 dated Aug. 28, 2007.
International Preliminary Report on Patentability dated Oct. 13, 2009 in International Application No. PCT/US2008/004708.
International Preliminary Report on Patentability for International Application No. PCT/US2008/012440 dated May 4, 2010.
International Preliminary Report on Patentability dated Jan. 12, 2012 in PCT/US2010/001794.
International Preliminary Report on Patentability (IPRP) (Chapter I) for PCT/US2011/000997, dated Dec. 4, 2012.
International Search Report and for International Application No. PCT/US2003/005521 dated Dec. 24, 2003.
International Search Report for International Application No. PCT/US2003/026424 dated Nov. 5, 2004.
International Search Report and Written Opinion for International Application No. PCT/US2006/006422 dated Oct. 19, 2006.
International Search Report and Written Opinion dated Jul. 22, 2008 for International Application No. PCT/US2008/004708.
International Search Report and Written Opinion for International Application No. PCT/US2008/012440 dated Mar. 25, 2009.
International Search Report and Written Opinion for International Application No. PCT/US2010/001794 dated Sep. 1, 2010.
International Search Report and Written Opinion for International Application No. PCT/US2011/000997 dated Sep. 9, 2011.
Ingall, T., "Stroke-Incidence, Mortality, Morbidity and Risk," *Journal of Insurance Medicine*, vol. 36, pp. 143-152, (2004).
Isler, O. et al., "Anwendung der Wittig-Reaktion zur Synthese von Estern des Bixins und Crocetins," *Helv. Chim. Acta*, vol. 40, No. 139, pp. 1242-1249, (1957); XP008042920.
Jansen, F.J.H.M., et al., "Synthesis and Characterization of All-E $(12,12'-^{13}C_2)$-, $(13,13'-^{13}C_2)$-, $(14,14'-^{13}C_2)$-, $(15,15'-^{13}C_2)$- and $(20,20'-^{13}C_2)$astaxanthin," *Recl. Trav. Chim. Pays-Bas*, vol. 113, p. 552-562, (1994).
Jiho, Inc., Design and Evaluation of Oral Formulation, pp. 337-339, (1995); No English Translation Available.
Johnson, M.E., et al., "Synergistic Effects of Chemical Enhancers and Therapeutic Ultrasound on Transdermal Drug Delivery," *Journal of Pharmaceutical Sciences*, vol. 85, No. 7, pp. 670-679, (1996).
Kalani, M., et al., "Hyperbaric Oxygen (HBO) Therapy in Treatment of Diabetic Foot Ulcers Long-term Follow-up," *Journal of Diabetes & Its Complications*, pp. 153-158, (2002).
Kamiryo, T. et al., "Histological Changes in the Normal Rat Brain After Gamma Irradiation," *Acta Neurochir* (Wien), vol. 138, pp. 451-459, (1996).
Kamiryo, T. et al., "Radiosurgery-induced Microvascular Alterations Precede Necrosis of the Brain Neuropil," *Neurosurgery*, vol. 49, No. 2, pp. 409-415, (2001).
Kichev, G.S. et al., "Experience of Using Perfluorane in Treating Critical Conditions of Various Geneses," *Medline.ru-Biomeditsinskii Zhurnal*, vol. 5, Art. 53, pp. 175-177, (2004); No English Translation Available.
Koynova, R., et al., "Modulation of Lipid Phase Behavior by Kosmotropic and Chaotropic Solutes—Experiment and Thermodynamic Theory," *Eur Biophys J*, vol. 25, pp. 261-274, (1997).
Laidig, K.E. et al., "Altering Diffusivity in Biological Solutions through Modification of Solution Structure and Dynamics," *Journal of the American Chemical Society*, vol. 120, No. 36, pp. 9394-9395, (1998); XP002970835.
Lancrajan, I., et al., "Carotenoid incorporation into natural membranes from artificial carriers: liposomes and beta-cyclodextrins," *Chemistry and Physics of Lipids*, vol. 112, pp. 1-10, (2001); XP55044152.
Lang, A.E., et al., "Parkinson's Disease," *New England Journal of Medicine*, vol. 339, No. 15, pp. 1044-1053, (1998).
Lapchak, P.A., et al., "Neuroprotective Effects of the Spin Trap Agent Disodium-[(tert-butylimino)methyl]benzene-1,3-disulfonate N-Oxide (Generic NXY-059) in a Rabbit Small Clot Embolic Stroke Model: Combination Studies With the Thrombolytic Tissue Plasminogen

(56) References Cited

OTHER PUBLICATIONS

Activator," *Stroke*, vol. 33, No. 5, pp. 1411-1415, (2002); DOI: 10.1161/01.STR.0000015346.00054.8B.

Lapchak, P.A., et al., "Comparison of Tenecteplase With Alteplase on Clinical Rating Scores Following Small Clot Embolic Strokes in Rabbits," *Experimental Neurology*, vol. 185, pp. 154-159, (2004); DOI: 10.1016/j.expneurol.2003.09.009.

Lapchak, P.A. et al., "Transcranial Infrared Laser Therapy Improves Clinical Rating Scores After Embolic Strokes in Rabbits," *Stroke*, vol. 35, No. 8, pp. 1985-1988, (2004); DOI: 10.1161/01.STR.0000131808.69640.b7.

Lapchak, P.A., "Memantime, an uncompetitive low affinity NMDA open-channel antagonist improves clinical rating scores in a multiple infarct embolic stroke model in rabbits," *Brain Research*, vol. 1088, No. 1, pp. 141-147, (2006); DOI: 10.1016/j.brainres.2006.02.093.

Lapchak, P.A., et al., "Advances in Ischemic Stroke Treatment: Neuroprotective and Combination Therapies," *Expert Opin. Emerging Drugs*, vol. 12, No. 2, pp. 1-16, (2007); DOI: 10.1517/14728214.12.2.

Lapchak, P.A., "The Phenylpropanoid Micronutrient Chlorogenic Acid Improves Clinical Rating Scores in Rabbits Following Multiple Infarct Ischemic Strokes: Synergism With Tissue Plasminogen Activator," *Experimental Neurology*, vol. 205, No. 2, pp. 407-413, (2007); DOI: 10.1016/j.expneurol.2007.02.017.

Lapchak, P.A., et al., "Transcranial Near-Infrared Light Therapy Improves Motor Function Following Embolic Strokes in Rabbits: An Extended Therapeutic Window Study Using Continuous and Pulse Frequency Delivery Modes," *Neuroscience*, vol. 148, pp. 907-914, (2007); DOI: 10.1016/j.neuroscience.2007.07.002.

Lapchak, P.A., et al., "Therapeutic Window for Nonerythropoietic carbamylated-erythropoietin to Improve Motor Function Following Multiple Infarct Ischemic Strokes in New Zealand White Rabbits," *Brain Research*, vol. 1238, pp. 208-214, (2008); DOI: 10.1016/j.brainres.2008.08.017.

Lapchak, P.A., "Efficacy and Safety Profile of the Carotenoid Trans Sodium Crocetinate Administered to Rabbits Following Multiple Infarct Ischemic Strokes: A Combination Therapy Study with Tissue Plasminogen Activator," *Brain Research*, vol. 1309, pp. 136-145, (2010), XP-002686117; DOI: 10.1016/j.brainres.2009.10.067.

Letham, D.S., et al., "The Synthesis of Radioisotopically Labelled Zeatin," *Phytochemistry*, vol. 10, pp. 2077-2081, (1971).

Lever, M., et al., "Some Ways of Looking at Compensatory Kosmotropes and Different Water Environments," *Comparative Biochemistry and Physiology, Part A*, vol. 130, pp. 471-486, (2001).

Lide, D.R. Ph.D., "CRC Handbook of Chemistry and Physics," *CRC Press*, 79th Edition, Boca Raton, FL, pp. 6-181, (1998).

Lishner, M., et al., "Treatment of Diabetic Perforating Ulcers (Mal Perforant) with Local Dimethylsulfoxide," *J. Am Geriatr Soc.*, vol. 33, No. 1, pp. 41-43, (1985).

Lyubimova, N., et al., "Experimental Evidence to Support the Hypothesis that Damage to Vascular Endothelium Plays the Primary Role in the Development of Late Radiation-induced CNS Injury," *The British Journal of Radiology*, vol. 77, pp. 488-492, (2004).

Maehara, Y., *Fukuoka Medical Journal*, vol. 88, No. 11, 1997, pp. 337-344; No English Translation Available.

Magazu, S., et al., "α,α-Trehalose-Water Solutions. VIII. Study of the Diffusive Dynamics of Water by High-Resolution Quasi Elastic Neutron Scattering," *J. Phys. Chem. B*, vol. 110, No. 2, pp. 1020-1025, (2006).

Magesh, V., "Studies on the anti-tumor effect of crocetin against benzo(a)pyrene induced lung cancer in Swiss albino mice," Biomedicine, (Chennai india) (Dec. 31, 2003), vol. 23 (3rd & 4th Edition), pp. 96-99, Database HCAPLUS on STN, DN 141:388250, Abstract.

Marx, R.E., D.D.S., "Osteoradionecrosis: A New Concept of its Pathophysiology," *J. Oral Maxillofac Surg*, vol. 41, pp. 283-288, (1983).

Marx, R.E., et al., "Relationship of Oxygen Dose to Angiogenesis Induction in Irradiated Tissue," *The American Journal of Surgery*, vol. 160, pp. 519-524, (1990).

Mayer, R., et al., "Hyperbaric Oxygen and Radiotherapy," *Strahlenther. Onkol.*, vol. 181, No. 2, pp. 113-123, (2005); DOI: 10.1007/s00066-005-1277-y.

Miyagawa, H., et al., "Pathogenesis of Delayed Radiation Injury in the Rat Spinal Cord After X-ray Irradiation," *Neuropathology*, vol. 16, pp. 126-132, (1996).

Moelbert, S., et al., "Kosmotropes and Chaotropes: Modeling Preferential Exclusion, Binding and Aggregate Stability," *Biophysical Chemistry*, vol. 112, pp. 45-57, (2004); DOI: 10.1016/j.bpc.2004.06.012.

Notification Concerning Transmittal of International Preliminary Report on Patentability (Chapter 1 of the Patent Cooperation Treaty) for International Application No. PCT/US2008/012440 dated May 14, 2010.

Ohga, E., et al., "The relationship between adhesion molecules and hypoxia," Nippon Rinsho, vol. 58, No. 8, pp. 1587-1591, (2000); No English Translation Available.

Okeda, R., "Pathological Changes in the Cerebral Medullary Arteries of Five Autopsy Cases of Malignant Nephrosclerosis: Observation by Morphometry and Reconstruction of Serial Sections," *Neuropathology*, vol. 23, pp. 153-160, (2003).

Okonkwo, D.O., et al., "Trans-sodium Crocetinate Increases Oxygen Delivery to Brain Parenchyma in Rats on Oxygen Supplementation," *Neuroscience Letters*, vol. 352, pp. 97-100, (2003).

Pastores, S.M., et al., "Posttraumatic Multiple-organ Dysfunction Syndrome: Role of Mediators in Systemic Inflammation and Subsequent Organ Failure," *Academic Emergency Medicine*, vol. 3, No. 6, pp. 611-622, (1996).

Pauling, L., "Recent Work on the Configuration and Electronic Structure of Molecules; with some Applications to Natural Products," *Fortschr. Chem. Org. Naturst.*, vol. 3, No. 303, pp. 203-235, (1939).

Pfander, H., et al., "Carotenoid Synthesis: A Progress Report," *Pure & Appl. Chem.*, vol. 69, No. 10, pp. 2047-2060, (1997).

Pfitzner, I., et al., "Carotenoid: methyl-β-cyclodextrin formulations: an improved method for supplementation of cultured cells," *Biochimica et Biophysica Acta*, vol. 1474, No. 2, pp. 163-168, (2000), XP004276552.

Pharmacia, vol. 27, No. 7, pp. 703-705, (1991); No English Translation Available.

Polyakov, N.E., et al., "Inclusion Complexes of Carotenoids with Cyclodextrins: $^1$H NMR, EPR, and Optical Studies," *Free Radical Biology & Medicine*, vol. 36, No. 7, pp. 872-880, (2004); XP27231510.

Re, R., et al., "Isomerization of Lycopene in the Gastric Milieu," *Biochemical and Biophysical Research Communications*, vol. 281, No. 2, pp. 576-581, (2001); DOI: 10.1006/bbrc.2001.4366.

RN: 120523-11-7; CN: 2,4,6,8,10, 12,14,16,18-Eicosanonaenedioic acid, 4,8, 13,17-tetramethyl-potassium sodium salt, (1989).

RN: 147484-59-1; CN: 2,4,6,8-Decatetraenedioic acid, disodium salt, (1993).

RN: 33261-80-2; CN: 2,4,6,8,10,12,14,16,18-Eicosanonaenedioic acid, 4,8,13,17-tetramethyl-dipotassium salt, (1984).

RN: 33261-81-3; CN: 2,4,6,8,10,12,14,16,18-Eicosanonaenedioic acid, 4,8,13,17-tetramethyl-disodium salt, (1984).

Rowinsky, E. K., "Novel Radiation Sensitizers Targeting Tissue Hypoxia," *Oncology*, vol. 13, No. 10, Supplement No. 5, pp. 61-70, (1999), XP009044613.

Roy, J.W., et al, "A Novel Fluid Resuscitation Therapy for Hemorrhagic Shock," *Shock*, vol. 10, No. 3, pp. 213-217, (1998).

Schwieter, U., et al., "Synthesen in der Carotinoid-Reihe 20. Mitteilung$^1$) Neue Synthesen von Apocarotinoiden," *Helvetica Chimica Acta*, vol. 49, pp. 369-390, (1966), XP-002575142.

Secor, R.M., "The Effect of Concentration on Diffusion Coefficient in Polymer Solutions," *A.I.Ch.E. Journal*, vol. 11, No. 3, pp. 452-456, (1965).

Seyde, W.C., et al., "Carotenoid Compound Crocetin Improves Cerebral Oxygenation in Hemorrhaged Rats," *Journal of Cerebral Blood Flow and Metabolism*, vol. 6, No. 6, pp. 703-707, (1986).

(56) References Cited

OTHER PUBLICATIONS

Shi, Nihon Butsuri Gakkai, "Structure and Function of Cartenoid in Photosynthetic System," *Journal of the Physical Society of Japan*, vol. 50, No. 7, pp. 555-561, (1995); No English Translation Available.

Singer, M., et al., "Intravenous Crocetinate Prolongs Survival in a Rat Model of Lethal Hypoxemia," *Crit Care Med*, vol. 28, No. 6, pp. 1968-1972, (2000).

Snyder, J.M., et al., "cis-trans Isomerization of Unsaturated Fatty Acids with p-Toluenesulfinic Acid," *J. Am. Oil Chem. Soc.*, vol. 59, No. 11, pp. 469-470, (1982).

Stennett, A.K., et al., "trans-Sodium Crocetinate and Diffusion Enhancement," *J. Phys. Chem. B.*, vol. 110, No. 37, pp. 18078-18080, (2006).

Streitwieser, A., et al., Introduction to Organic Chemistry, 2nd Ed., pp. 504-505, (1981).

The Lung perspectives, vol. 9, No. 2, pp. 161-165, (2001); No English Translation Available.

Tong, L., "Cyclodextrins Chemistry: Fundamentals and Application," *Science Press*, pp. 360-364, (2001); No English Translation Available.

Tyssandier, V., et al., "Processing of Vegetable-borne Carotenoids in the Human Stomach and Duodenum," *Am J Physiol Gastrointest Liver Physiol*, vol. 284: G913-G923, (2003).

Vickackaite, V., et al., "Photochemical and Thermal Degradation of a Naturally Occuring Dye Used in Artistic Painting. A Chromatographic, Spectrophotometric and Fluorimetric Study on Saffron," *International Journal of Photoenergy*, vol. 6, pp. 175-183, (2004).

Wang, Y., et al., "The Effect of Trans-Sodium Crocetinate in a Model of Intracranial Hemorrhage," Abstracts of the Annual Meeting of the Society for Neuroscience, Society for Neuroscience Abstract Viewer and Itinerary Planner, 2 pages, (Nov. 15, 2008) Washington, DC, XP009163975.

Wenkert, E., et al., "Polyene Synthesis. Ready Construction of Retinol-Carotene Fragments (±)-6-(E)-LTB, Leukotrienes, and Corticrocin," *Journal of Organic Chemistry*, vol. 55, No. 25, pp. 6203-6214, (1990), XP002317164.

White, D.C., "The Histopathologic Basis for Functional Decrements in Late Radiation Injury in Diverse Organs," *Cancer*, vol. 37, No. 2, pp. 1126-1143, February Supplement, (1976).

Widmer, E., et al., "Technical Procedures for the Syntheses of Carotenoids and Related Compounds from 6-Oxo-isophorone: Syntheses of (3R.3R)-Zeaxanthin," *Helvetica Chemica Acta*, vol. 73, pp. 861-867, (1990).

Wilkins, E.S., et al., "The Effect of Crocetin on the Irradiation of Walker-256: In Vitro and In Vivo Studies," *Cancer Biochem. Biophys.*, vol. 3, pp. 71-74, (1979), XP008157982.

Williamson, R.A., "An Experimental Study of the Use of Hyperbaric Oxygen to Reduce the Side Effects of Radiation Treatment for Malignant Disease," *Int. J. Oral Maxillofac. Surg.*, vol. 36, pp. 533-540, (2007).

Wirz, R., et al., "Celluloseaffinität von Polyendicarbonsäuren vom Typ des Crocetins und von quarternären Ammoniumverbindungen," *Helv. Chim. Acta*, vol. 63, No. 6, pp. 1738-1745, (1960), XP008042762.

Wurtman, R.J., "Alzheimer's Disease," *Scientific American*, vol. 252, (1985).

Yamaguchi, K., et al., "Kinetics of $O_2$ Uptake and Release by Human Erythrocytes Studied by a Stopped-flow Technique," *The American Physiological Society*, vol. 58, pp. 1215-1224, (1985).

Zheng, S., et al., "Crocetin Attenuates Atherosclerosis in Hyperlipidemic Rabbits Through Inhibition of LDL Oxidation," *J. Cardiovasc. Pharrnacol*, vol. 47, No. 1, pp. 70-76, (2006); XP009135396, ISSN: 0160-2446.

Search Report dated Sep. 15, 2015, issued in Chinese Patent Application No. 201080027664.7 and English translation.

Search Report dated Dec. 14, 2015, issued in Chinese Application No. 201180033875.6, which corresponds to PCT/US2011/000997, and English translation.

Search Report dated Oct. 21, 2016, issued in Chinese Application No. 201510128602.X, which is a national phase of PCT/US2006/006422, and English translation.

Supplementary Partial European Search Report dated Feb. 25, 2005 based on Application No. EP 03 71 1221.

Supplementary Partial European Search Report dated Apr. 21, 2005 based on Application No. EP 03 71 1221.

Supplementary Partial European Search Report dated Nov. 7, 2006.

Supplementary European Search Report dated Apr. 29, 2010 issued by the European Patent Office in one of Applicants' corresponding foreign applications.

Supplementary European Search Report dated Dec. 8, 2010 (corresponding to applicant's European Regional Phase Patent Application No. EP 08844993.9 based on International Patent Application No. PCT/US2008/012440 filed on Oct. 31, 2008).

Supplementary European Search Report dated Oct. 29, 2012 issued by the European Patent Office and Preliminary Opinion.

Supplementary Extended European Search Report dated Nov. 21, 2012 issued by the European Patent Office and Preliminary Opinion.

Supplementary (Extended) European Search Report dated Oct. 21, 2013 in European Patent Application No. EP 11790107.4 issued from PCT/US2011/000997 filed on Jun. 2, 2011, together with the Written Opinion.

Supplementary Extended European Search Report dated Mar. 28, 2013 issued by the European Patent Office and Written Opinion.

Australian Office Action dated Jun. 25, 2008 from corresponding Australian Patent Office.

Australian Office Action dated Mar. 26, 2010 in Applicant's Australian Application No. 2003265617.

Australian Office Action dated Oct. 25, 2010 issued by the Australian Patent Office in one of Applicants' corresponding foreign applications.

Australian Office Action dated Dec. 23, 2011.

Australian Office Action dated Dec. 3, 2014 from the Australian Patent Office for applicant's Australian application corresponding to PCT Application No. PCT/US03/26424.

Australian Office Action dated Dec. 10, 2014 from applicant's Australian application corresponding to PCT Application No. PCT/US2008/012440.

Australian Office Action dated Feb. 25, 2015 from applicant's application corresponding to PCT Application No. PCT/US2011/000997.

Australian Examination Report No. 1 dated Dec. 1, 2016, issued in Australian Patent Application No. 2016201192, which is a National Phase of PCT/US2011/000997.

Canadian Office Action dated Mar. 26, 2013, for applicant's Canadian Patent Application No. 2,598,882 corresponding to PCT/US06/006422 filed Feb. 24, 2006.

Canadian Office Action dated May 30, 2013, for applicant's Canadian Patent Application No. 2,683,760 corresponding to PCT/US2008/004708 filed Apr. 11, 2008.

Canadian Office Action dated Oct. 20, 2009 from Canadian Application No. 2,477,245.

Canadian Office Action issued Jul. 7, 2010 in corresponding Canadian Application No. 2,477,245.

Canadian Office Action issued Oct. 26, 2010 in corresponding Canadian Application No. 2,537,210.

Canadian Office Action dated Jul. 5, 2011 in corresponding Canadian Application No. 2,537,210.

Canadian Office Action dated Nov. 4, 2014 in Canadian Patent Application No. 2,703,946 from national phase of PCT/US2008/012440.

Canadian Office Action dated Apr. 12, 2016, issued in Canadian Patent Application No. 2,765,697, which is the national phase of PCT/US2010/001794.

Canadian Office Action dated Aug. 3, 2016, issued in Canadian Patent Application No. 2,703,946, which corresponds to PCT/US2008/012440.

Canadian Office Action dated Aug. 31, 2016, issued in Canadian Patent Application No. 2,598,882, which is the national phase of PCT/US2006/06422.

(56) References Cited

OTHER PUBLICATIONS

Chinese Office Action dated Nov. 7, 2008 in a corresponding application owned by the applicants in Chinese Application No. 03826969.4.
Chinese Third Office Action in Chinese Patent Application No. 03804566.4 dated Jan. 23, 2009 (English Translation Only).
Chinese Office Action and its English Translation dated Feb. 12, 2010 in the Assignee's Chinese application relating to PCT/US2006/006422.
Chinese Office Action dated Mar. 29, 2010 from Chinese Patent Application No. 03826969.4 based on PCT/US2003/026424.
Chinese Office Action and its English Translation dated Feb. 21, 2011 in Assignee's Chinese Patent Application No. 200680013663.0 based on PCT/US2006/006422.
Chinese Office Action and its English Translation dated Apr. 6, 2011 from Chinese Patent Application No. 200680013663.0 based on PCT/US2006/006422.
Chinese Office Action and its English Translation dated Jun. 30, 2011 in Chinese Application No. 2008801143109 (English Translation Only).
Chinese Office Action and its English Translation dated Jan. 18, 2012 in Chinese Patent Application No. 200680013663.0 based on PCT/US2006/006422 (English Translation Only).
Chinese Office Action and its English translation dated May 3, 2012, from Chinese Patent Application No. 03804566.4 based on PCT/US2003/005521.
Chinese Office Action and its English translation dated Jun. 6, 2012, from Chinese Patent Application No. 200880015671.8 based on PCT/US2008/004708.
Chinese Office Action and its English Translation dated Jun. 14, 2012 from Chinese Patent Application No. 200880114310.9 that corresponds to PCT/US2008/012440.
Chinese Office Action and its English Translation dated Jan. 28, 2013, from Chinese Patent Application No. 200880015671.8 that corresponds to PCT/US2008/004708.
Chinese Patent Office Decision of Rejection dated May 2, 2013 and its English translation, corresponding to PCT/US2006/06422 filed on Feb. 24, 2006.
Chinese Office Action dated May 6, 2013, from Chinese Patent Application No. 201080027664.7 that corresponds to PCT/US2010/001794, and its English translation.
Chinese Office Action dated Jul. 9, 2013, from Chinese Patent Application No. 200880114310.9 that corresponds to PCT/US2008/012440, and its English translation.
Chinese Office Action and its English translation dated Nov. 1, 2013, from Chinese Patent Application No. 201180033875.6 that corresponds to PCT/US2011/000997.
Chinese Office Action and its English translation dated Mar. 19, 2014, from Chinese Patent Application No. 200880015671.8 that corresponds to PCT/US2008/004708.
Chinese Office Action and its English translation dated Mar. 31, 2014, from Chinese Patent Application No. 201210063676.6 that corresponds to PCT/US2003/026424, filed Aug. 25, 2003.
Chinese Office Action and English Translation dated Jul. 21, 2014 issued in Chinese Patent Application No. 200680013663.0, 9 pp.
Chinese Office Action and English Translation dated Jul. 24, 2014 issued in Chinese Patent Application No. 200880114310.9, 19 pp.
Chinese Office Action dated Aug. 15, 2014 issued in Chinese Patent Application No. 201080027664.7 and English Translation, 13 pp.
Chinese Office Action and English Translation dated Dec. 8, 2014 (Reexamination Decision) from the Chinese Patent Office in applicant's Chinese Application corresponding to PCT Application No. PCT/US06/06422.
Chinese Notice and Office Action and English Translations dated Dec. 22, 2014 from the China Patent Office for applicant's China application corresponding to PCT Application No. PCT/US2011/000997 (English Translation Only).
Chinese Office Action and its English translation dated May 5, 2015 for national phase of PCT/US2008/004708.
Chinese Office Action and its English translation dated Jun. 24, 2015 for National Phase of PCT/US03/26424 (with translation).
Chinese Fifth Notification of Office Action dated Aug. 17, 2015, issued in Chinese Patent Application No. 200880114310.9 and English translation.
Chinese Third Notification of Office Action dated Sep. 25, 2015, issued in Chinese Patent Application No. 201080027664.7 and English translation.
Chinese Third Notification of Office Action dated Dec. 14, 2015, issued in Chinese Application No. 201180033875.6, which corresponds to PCT/US2011/000997, and English translation.
Chinese Fifth Notification of Office Action dated Jun. 21, 2016, issued in Chinese Patent Application No. 200880015671.8, which is the national phase of PCT/US2008/04708, and English translation.
Chinese Sixth Notification of Office Action dated Aug. 16, 2016, issued in Chinese Patent Application No. 200880114310.9, which is the national phase of PCT/US2008/012440, and English translation.
Chinese First Notification of Office Action dated Oct. 31, 2016, issued in Chinese Application No. 201510128602.X, which is a National Phase of PCT/US2006/006422, and English translation.
Chinese Decision of Rejection dated Nov. 10, 2016, issued in Chinese Application No. 201080027664.7, which is a National Phase of PCT/US2010/001794, and English translation.
Chinese Decision for Rejection and its English Translation dated Nov. 28, 2016 issued in Chinese Patent Application No. 201180033875.6 which is a national phase of PCT/US2011/000997.
Chinese Search Report dated Mar. 18, 2013, and its English translation.
Chinese Search Report dated Jun. 27, 2013, and its English translation.
Chinese Search Report and its English translation dated Mar. 19, 2014, from Chinese Patent Application No. 201210063676.6 that corresponds to PCT/US2003/026424, filed Aug. 25, 2003.
Chinese Search Report dated Oct. 21, 2016, issued in Chinese Application No. 201510128602.X, which is a national phase of PCT/US06/06422, and English translation.
Eurasian Patent Office Action and its English translation dated Nov. 9, 2011.
Eurasian Patent Office Action and its English translation dated Nov. 17, 2011.
European Office Action dated Nov. 9, 2009 in Applicant's European application corresponding to PCT/US2003/005521.
European Office Action dated Nov. 9, 2009 in Applicant's European application corresponding to PCT/US2003/026424.
European Office Action dated Apr. 7, 2011, from European Patent Application No. EP 08742781.1.
European Office Action dated Oct. 17, 2011 from European Patent Application No. EP 08742781.1.
European Office Action dated Oct. 31, 2011, from European Patent Application No. EP 06758166.0.
European Office Action dated Apr. 25, 2012, from European Patent Application No. 08844993.9.
European Office Action dated Jun. 11, 2012, from European Patent Application No. EP 08742781.1.
European Office Action dated Mar. 12, 2014, from applicant's European Patent Application No. EP 12166293.6, corresponding to PCT/US2006/006422 filed Feb. 24, 2006.
European Office Action dated Nov. 21, 2014 from the EPO for applicant's EP Application No. 03818748.0 based on PCT/US2003/26424.
European Office Action dated Feb. 2, 2015 from the for applicant's application corresponding to PCT Application No. PCT/US2008/012440.
European Office Action dated Feb. 2, 2015 from the for applicant's application corresponding to PCT Application No. PCT/US03/05521.
European Office Action dated Oct. 27, 2015 that issued in the European application that corresponds to PCT//US03/05521.
European Communication pursuant to Article 94(3) EPC dated May 17, 2016, issued in European Patent Application No. 03 711 221.6, which is the national phase of PCT/US03/05521.

(56) References Cited

OTHER PUBLICATIONS

European Communication pursuant to Article 94(3) EPC dated May 19, 2016, issued in European Patent Application No. 03 818 748.0, which is the national phase of PCT/US03/26424.
European Communication pursuant to Article 94(3) EPC dated Jun. 3, 2016, issued in European Patent Application No. 11 790 107.4, which is the national phase of PCT/US2011/000997.
European Communication Pursuant to Article 94(3) EPC dated Jul. 6, 2016, issued in European Patent Application No. 12 166 293.6, which is the national phase of PCT/US2006/006422.
Hungarian Novelty Search Report dated Nov. 5, 2009 (w/translation).
India Office Action dated Oct. 23, 2008 in a corresponding application owned by the applicants (India Patent App No. 676/DELNP/2006).
India Examination Report dated Apr. 12, 2010 issued by the India Patent Office in one of Applicants' corresponding foreign applications.
India Office Action (Examination Report) dated Feb. 21, 2013, for applicant's India Patent Application No. 6688/DELNP/2007 corresponding to PCT/US2006/006422 filed Feb. 24, 2006.
India Office Action dated Dec. 31, 2014 from the India Patent Office for applicant's India application corresponding to PCT Application No. PCT/US2008/04708.
India Office Action dated Jul. 21, 2015 for National Phase of PCT/US2003/26424.
India Office Action dated Jul. 23, 2015 for National Phase of PCT/US2008/012440.
India Office Action dated Aug. 23, 2016, issued in Indian Patent Application No. 6834/DELNP/2009, which is the national phase of PCT/US2008/04708.
Israeli Office Action dated Apr. 10, 2013, from applicant's Israel Patent Application No. 185460 corresponding to PCT/US06/06422 filed Feb. 24, 2006, and its English translation.
Israeli Office Action issued Oct. 29, 2013, from Israel Patent Application No. 201438 that corresponds to PCT/US2008/004708, and its English translation.
Israeli Office Action and English Translation dated May 4, 2014 from applicant's Israel Patent Application No. 185460 corresponding to PCT/US06/06422 filed Feb. 24, 2006.
Israeli Office Action dated Feb. 1, 2015 for applicant's application corresponding to PCT Application No. PCT/US2003/026424.
Israeli Office Action dated Dec. 30, 2015, issued in Israeli Patent Application No. 216919, which corresponds to PCT/US2010/001794, and English translation.
Japanese Patent Office Action dated Jun. 2, 2009 and its English translation, cited in one of Assignee's Japanese Patent Application No. 2003-571422.
Japanese Patent Office Action dated Jun. 9, 2009 and its English translation, cited in one of Assignee's Japanese patent applications.
Japanese Decision of Rejection dated Jan. 12, 2010 and its English translation, corresponding to PCT/US2003/005521 corresponding to Diffusion's U.S. Pat. No. 7,351,844.
Japanese Office Action and its English Translation dated Jan. 12, 2010 in the Assignee's Japanese application relating to PCT/US2003/026424.
Japanese Office Action and its English Translation dated Apr. 6, 2010 in the Assignee's Japanese application relating to PCT/US2006/006422.
Japanese Notice of Reasons for Rejection and its English Translation dated May 24, 2011 issued in Japanese Patent Appln. No. 2007-557157 (corresponding to PCT/US2006/006422).
Japanese Office Action and its English Translation dated Oct. 4, 2011.
Japanese Office Action and its English Translation dated Jul. 10, 2012 for Applicant's Japanese Patent Application No. 2009-274988 corresponding to PCT/US2003/005521, filed Feb. 25, 2003.
Japanese Decision of Rejection dated May 21, 2013, from applicant's Japanese Patent Application No. 2010-110185 corresponding to PCT/US2003/05521 filed Feb. 25, 2003, and its English translation.
Japanese Office Action (Notice of Reasons for Rejection) and its English translation dated Jun. 4, 2013, from applicant's Japanese Patent Application No. 2011-209754 corresponding to PCT/US06/06422 filed Feb. 24, 2006.
Japanese Office Action (Final Rejection) and its English translation dated Sep. 10, 2013, from applicant's Japanese Application No. P2009-279890 corresponding to PCT/US03/26424 filed Aug. 25, 2003.
Japanese Office Action (Final Rejection) and its English translation dated Nov. 26, 2013, from applicant's Japanese Application No. P2010-503069 corresponding to PCT/US08/004708 filed Apr. 11, 2008.
Japanese Office Action (Final Rejection) and its English translation dated Feb. 4, 2014 from applicant's Japanese Application No. P2011-209754 corresponding to PCT/US06/06422 filed Feb. 24, 2006.
Japanese Office Action and its English translation dated Apr. 22, 2014 from applicant's Japanese Application No. P2010-531078 corresponding to PCT/US08/012440 filed Oct. 31, 2008.
Japanese Office Action dated Jun. 24, 2014 issued in Japanese Patent Application No. P2012-516071 and English Translation, 10 pp.
Japanese Office Action and its English translation dated Sep. 9, 2014 issued in Japanese Patent Application No. P2010-531078, 6 pp.
Japanese Office Action and English Translation dated Sep. 9, 2014 issued in Japanese Patent Application No. 2013-197629, 6 pp.
Japanese Office Action and English translation dated Sep. 24, 2014 issued in Japanese Patent Application No. P2011-209754, 5 pp.
Japanese Office Action dated Jan. 27, 2015 from the for applicant's application corresponding to PCT Application No. PCT/US03/26424.
Japanese Office Action and its English translation dated Apr. 14, 2015 for national phase of PCT/US2008/012440.
Japanese Office Action and its English translation dated Apr. 21, 2015 for national phase of PCT/US2008/04708.
Japanese Office Action and its English translation dated Apr. 21, 2015 for national phase of PCT/US2011/000997.
Japanese Final Rejection dated Nov. 24, 2015, issued in Japanese Patent Application No. P2013-513151, which corresponds to PCT/US2011/000997, and English translation.
Japanese Notice of Reasons for Rejection dated Nov. 24, 2015, issued in Japanese Patent Application No. P2015-011575, which corresponds to PCT/US2006/006422, and English translation.
Japanese Final Rejection dated Mar. 1, 2016, issued in Japanese Patent Application No. P2014-061897, which corresponds to PCT/US2008/004708, and English translation.
Japanese Notice of Reasons for Rejection dated Jun. 21, 2016, issued in Japanese Patent Application No. 2015-159872 and English translation.
Japanese Final Rejection dated Jun. 28, 2016, issued in Japanese Patent Application No. 2015-011575, which is the national phase of PCT/US2006/006422, and English translation.
Korean Office Action dated May 26, 2009, and English translation in a corresponding application owned by the applicants.
Korean Office Action dated Nov. 23, 2009 in applicant's corresponding Korean application No. 10-2006-7003827.
Korean Office Action and its English Translation dated Jun. 22, 2010 from Applicant's Korean Patent Appln. No. 10-2006-7003827, that corresponds to PCT/US2003/026424.
Korean Office Action and its English Translation dated Jul. 6, 2010 in the Assignee's Korean Application No. 10-2004-17013118, that is the Nationalized Appln. from PCT/US03/005521, claiming priority from U.S. Appl. No. 60/358,718.
Korean Office Action and English Translation dated Jul. 28, 2014 issued in Korean Patent Application No. 10-2009-7023432, 8 pp.
Korean Office Action dated Jan. 16, 2015 from the South Korea Patent Office for applicant's application corresponding to PCT Application No. PCT/US2008/012440.

(56) References Cited

OTHER PUBLICATIONS

Korean Office Action dated May 27, 2015 and its English translation for Application. No. 10-2009-7023432 (national phase of PCT/US2008/04708).
Korean Notice of Preliminary Rejection dated Nov. 24, 2015, issued in Korean Application No. 10-2010-7010445, which corresponds to PCT/US2008/012440, and English translation.
Korean Notice of Preliminary Rejection dated Jul. 26, 2016, issued in South Korean. Patent Application No. 10-2012-7001265, which is the national phase of PCT/US2010/001794, and English translation.
Mexican Office Action dated Feb. 23, 2009 in a corresponding application owned by the applicants in Mexican Patent Appln. No. PA/a/2004/008253.
Mexican Office Action dated May 2010, and its English translation of rejected parts of the Office Action, from Mexican Patent Application No. PA/a/2004/008253 corresponding to International Patent Application No. PCT/EP2003/005521.
Mexican Office Action and its English translation dated Oct. 20, 2011.
New Zealand Examination Report dated Jan. 8, 2008 from corresponding New Zealand Patent Office.
New Zealand Examination Report dated Oct. 6, 2008 issued by the New Zealand Patent Office in one of Applicants' corresponding foreign applications.
New Zealand Examination Report dated Jul. 2, 2009 issued by the New Zealand Patent Office in one of Applicants' corresponding foreign applications.
New Zealand Examination Report dated Apr. 7, 2010 issued by the New Zealand Patent Office in Applicants' corresponding foreign Application No. 584433.
New Zealand Examination Report dated Oct. 7, 2010 issued by the New Zealand Patent Office in one of Applicants' corresponding foreign applications.
New Zealand Examination Report dated Jan. 21, 2011.
New Zealand Examination Report dated Oct. 2011 issued by the New Zealand Patent Office in Applicants' corresponding foreign Application No. 595624.
Norwegian Office Action and its English Translation dated Jun. 22, 2010 in the Assignee's Norwegian application relating to PCT/US2003/005521.
Norwegian Office Action and its English Translation dated Feb. 16, 2011, from Norway Patent Application No. 20043661, based on International Patent Application No. PCT/US2008/012440.
Polish Office Action dated Feb. 23, 2010 from Polish Patent Application No. P-373780 based on PCT/US2003/005521.
Polish Office Action dated Sep. 2010 in corresponding Polish Application No. P-373780.
Ukraine Office Action dated Aug. 2010.
U.S. Final Office Action dated Dec. 4, 2008 from U.S. Appl. No. 11/361,054, 6 pages.
U.S. Non-Final Office Action dated Aug. 24, 2007, in U.S. Appl. No. 11/790,779, 6 pages.
U.S. Non-Final Office Action dated Sep. 28, 2007, in U.S. Appl. No. 11/723,383, 5 pages.
U.S. Non-Final Office Action dated Nov. 13, 2008, in U.S. Appl. No. 10/647,132, 7 pages.
U.S. Non-Final Office Action dated Oct. 28, 2009, in U.S. Appl. No. 11/361,054, 5 pages.
U.S. Non-Final Office Action dated Sep. 22, 2011, in U.S. Appl. No. 11/790,779, 8 pages.
U.S. Non-Final Office Action dated Dec. 19, 2011 in U.S. Appl. No. 12/801,726, 7 pages.
U.S. Non-Final Office Action dated Jan. 4, 2012 in U.S. Appl. No. 13/137,337, 5 pages.
U.S. Non-Final Office Action dated Jan. 24, 2012 in U.S. Appl. No. 13/137,322, 9 pages.
U.S. Non-Final Office Action dated Mar. 16, 2012 in U.S. Appl. No. 13/137,324, 5 pages.
U.S. Non-Final Office Action dated May 10, 2012 in U.S. Appl. No. 13/067,469, 17 pages.
U.S. Final Office Action dated Jul. 26, 2012 in U.S. Appl. No. 12/801,726, 6 pages.
U.S. Non-Final Office Action dated Sep. 6, 2012 in U.S. Appl. No. 13/137,322, 9 pages.
U.S. Final Office Action dated Sep. 18, 2012 in U.S. Appl. No. 13/137,337, 5 pages.
U.S. Final Office Action dated Dec. 24, 2012 in U.S. Appl. No. 13/137,324, 10 pages.
U.S. Final Office Action dated Jan. 15, 2013 from U.S. Appl. No. 13/067,469, 21 pages.
U.S. Final Office Action dated Apr. 5, 2013 from U.S. Appl. No. 13/137,322, 10 pages.
U.S. Final Office Action dated Jun. 12, 2013 from U.S. Appl. No. 12/801,726, 6 pages.
U.S. Advisory Office Action dated Jul. 16, 2013 in U.S. Appl. No. 13/137,324, 7 pages.
U.S. Non-Final Office Action dated Jul. 29, 2013 from U.S. Appl. No. 13/067,469, 21 pages.
U.S. Non-Final Office Action dated Aug. 22, 2013 from U.S. Appl. No. 13/507,365, 6 pages.
U.S. Final Office Action dated Nov. 20, 2013 in U.S. Appl. No. 13/137,337, 5 pages.
U.S. Non-Final Office Action dated Dec. 6, 2013 from U.S. Appl. No. 13/137,322, 8 pages.
U.S. Non-Final Office Action dated Jan. 30, 2014 from U.S. Appl. No. 12/801,726, 5 pages.
U.S. Final Office Action dated May 8, 2014 from U.S. Appl. No. 13/507,365, 5 pages.
U.S. Non-Final Office Action dated Jun. 5, 2014 from U.S. Appl. No. 13/067,469, 26 pages, Gainer.
U.S. Non-Final Office Action dated Jun. 9, 2014 from U.S. Appl. No. 13/137,324, 7 pages, Gainer et al.
U.S. Non-Final Office Action dated Jun. 26, 2014 in U.S. Appl. No. 13/137,337, 5 pages.
U.S. Final Office Action dated Sep. 8, 2014 issued in U.S. Appl. No. 12/801,726, 23 pages.
U.S. Non-Final Office Action dated Oct. 1, 2014 issued in U.S. Appl. No. 13/621,650, 51 pages.
U.S. Final Office Action dated Nov. 25, 2014 in U.S. Appl. No. 13/067,469, 13 pages.
U.S. Non-Final Office Action dated Dec. 8, 2014 in U.S. Appl. No. 13/137,324, 11 pages.
U.S. Non-Final Office Action dated Dec. 29, 2014 in U.S. Appl. No. 13/507,365, 5 pages.
U.S. Non-Final Office Action dated Apr. 29, 2015, in U.S. Appl. No. 12/801,726, 6 pages.
U.S. Final Office Action dated Jun. 4, 2015 for U.S. Appl. No. 13/621,650, 6 pages.
U.S. Final Office Action dated Jul. 9, 2015 for U.S. Appl. No. 13/137,324, 6 pages.
U.S. Final Office Action dated Aug. 13, 2015 for U.S. Appl. No. 13/507,365, 5 pages.
U.S. Non-Final Office Action dated Sep. 30, 2015 in U.S. Appl. No. 13/137,337, 4 pages.
U.S. Final Office Action dated Nov. 12, 2015 for U.S. Appl. No. 12/801,726, 6 pages.
U.S. Non-Final Office Action dated Mar. 16, 2016 for U.S. Appl. No. 13/507,365, 4 pages.
U.S. Non-Final Office Action dated May 5, 2016, issued in U.S. Appl. No. 12/801,726, which corresponds to PCT/US2010/001794, 6 pages.
U.S. Final Office Action dated Nov. 14, 2016, issued in U.S. Appl. No. 12/801,726, which corresponds to PCT/US2010/001794, 11 pages.
Japanese Office Action and its English Translation dated Jul. 10, 2012 from Japanese Application No. 2009-279890 based on PCT/US2003/026424.
Japanese Office Action (Notice of Reasons for Rejection) dated Jan. 29, 2013, for applicant's Japanese Patent Application No. 2010-503069 corresponding to PCT/US08/004708 filed Apr. 11, 2008, and its English translation.

(56) References Cited

OTHER PUBLICATIONS

Japanese Patent Office Action dated Feb. 19, 2013, from applicant's Japanese Patent Application No. 2009-279890 corresponding to PCT/US03/26424 filed Aug. 25, 2003, and its English translation.
Japanese Office Action (Reasons for Rejection) dated Jun. 18, 2013, in Japanese App. No. 2010-531078 (no English translation).
Japanese Official Action dated Sep. 8, 2015.
Japanese Office Action dated Jan. 12, 2016, issued in Japanese Patent Application No. 2014-003614, which corresponds to PCT/US2003/026424.
Korean Patent Office Action dated Sep. 26, 2012, from Korean Patent Application No. 10-2007-7021197 based on PCT/US2006/006422, and its English translation.
Mexican Office Action dated Aug. 27, 2012, corresponding to U.S. Appl. No. 12/081,236, filed Apr. 11, 2008 (No English Translation Available).
U.S. Non-Final Office Action dated Oct. 12, 2016, issued in U.S. Appl. No. 14/642,703, which corresponds to PCT/US2011/000997, 15 pages.
Gainer, J.L., et al, "Trans Sodium Crocetinate with Temozolomide and Radiation Therapy for Glioblastoma Multiforme," J Neurosurg, vol. 126, pp. 460-466, (2017), Published online May 13, 2016; doi: 10.3171/2016.3.JNS152693.
Mohler III, E.R., et al., "Evaluation of Trans Sodium Crocetinate on Safety and Exercise Performance in Patients with Peripheral Artery Disease and Intermittent Claudication," NIH Public Access, Author Manuscript, available in PMC 2014, 14 pages, doi: 10.1177/1358863X11422742, face of article states: Published in final edited form as: Vasc Med. Oct. 2011; 16(5), 346-353.
Murray, R., "Pharmacokinetics of TSC and the Treatment of Hypoxic States," A Dissertation Presented to the Faculty of the School of Engineering and Applied Science, University of Virginia, 106 pages, retrieved on Sep. 5, 2019, from: https://media.proquest.com/media/pq/classic/doc/888859001/fmt/ai/rep/SPDF?_s=eOSFva3r5jHJaP4%2FUSCxt3i9uLU%3D.
Stennett, A. et al., "Trans-Sodium Crocetinate and Hemorrhagic Shock," Shock, vol. 28, No. 3, pp. 339-344, (2007).
Stennett, A., "Mechanism of Action of TSC," A Dissertation Presented to the Faculty of the School of Engineering and Applied Science, University of Virginia, 191 pages, retrieved on Sep. 5, 2019, from: https://media.proquest.com/media/pq/classic/doc/888858991/fmt/ai/rep/SPDF?_s=RXVfuP3SH6vxf1TE4SVMciZ8bfc%3D.
Clinical Trials.gov, "Trans Sodium Crocetinate (TSC) Study of Intra-tumoral Oxygen Concentration, Safety, and Pharmacokinetics in Patients With High Grade Glioma," ClinicalTrials.gov Identifier: NCT00826930, 7 pages, retrieved on Nov. 27, 2019, from: https://clinicaltrials.gov/ct2/show/NCT00826930.
ClinicalTrials.gov, "Safety and Efficacy of Trans Sodium Crocetinate (TSC) With Radiation and Temozolomide in Newly Diagnosed Glioblastoma," ClinicalTrials.gov Identifier: NCT01465347, 9 pages, retrieved on Nov. 27, 2019, from: https://clinicaltrials.gov/ct2/show/NCT01465347.
Bazan, N., et al., "Hypoxia Signaling to Genes," Molecular Neurobiology, vol. 26, Nos. 2-3, pp. 283-298, (2002).
Beauchesne, P. et al., "Prolonged Survival for Patients with Newly Diagnosed, Inoperable Glioblastoma with 3-Times Daily Ultrafractionated Radiation Therapy," Neuro-Oncology, vol. 12, No. 6, pp. 595-602, (2010).
Bosco, G. et al., "Effect of Hyperbaric Oxygenation and Gemcitabine on Apoptosis of Pancreatic Ductal Tumor Cells In Vitro," Anticancer Research, vol. 33, pp. 4827-4832, (2013).

Hepple, R. et al., "No Effect of Trans Sodium Crocetinate on Maximal $O_2$ Conductance or $V_{O2,max}$ in Moderate Hypoxia," Respiratory Physiology & Neurobiology, vol. 134, pp. 239-246, (2003).
Kole, A. et al., "Concurrent Chemoradiotherapy Versus Radiotherapy Alone for 'Biopsy-Only' Glioblastoma Multiforme," Cancer, vol. 122, pp. 2364-2370, (2016).
Manabe, H. et al., "Metabolic Reflow as a Therapy for Ischemic Brain Injury," Acta Neurochirurgica Supplementum, vol. 110/2, pp. 87-91, (2011).
Manabe, H. et al., "Protection Against Focal Ischemic Injury to the Brain by Trans-Sodium Crocetinate: Laboratory Investigation," NIH Public Access, Author Manuscript, available in PMC 2012, 18 pages, doi: 10.3171/2009.10.JNS09562, face of article states: Published in final edited form as: *J Neurosurg*. Oct. 2010; 113(4):802-809.
Ogawa, K. et al., "Phase II Trial of Radiotherapy After Hyperbaric Oxygenation with Multiagent Chemotherapy (Procarbazine, Nimustine, and Vincristine) for High-Grade Gliomas: Long-Term Results," International Journal of Radiation, Oncology, Biology, Physics, vol. 82, No. 2, pp. 732-738, (2012).
Redenti, E., et al., "Cyclodextrin Complexes of Salts of Acidic Drugs. Thermodynamic Properties, Structural Features, and Pharmaceutical Applications," Journal of Pharmaceutical Sciences, vol. 90, No. 8, pp. 979-986, (2001).
Sheehan, J. et al., "Use of Trans Sodium Crocetinate for Sensitizing Glioblastoma Multiforme to Radiation," J Neurosurg., vol. 108, pp. 972-978, (2008).
Sheehan, J. et al., "Effect of Trans Sodium Crocetinate on Brain Tumor Oxygenation: Laboratory Investigation," J Neurosurg., vol. 111, pp. 226-229, (2009).
Sheehan, J. et al., "Trans-sodium Crocetinate Enhancing Survival and Glioma Response on Magnetic Resonance Imaging to Radiation and Temozolomide: Laboratory Investigation," J Neurosurg., vol. 113, pp. 234-239, (2010).
Sheehan, J. et al., "Trans Sodium Crocetinate: Functional Neuroimaging Studies in a Hypoxic Brain Tumor: Laboratory Investigation," J Neurosurg., vol. 115, pp. 749-753, (2011).
Stupp, R. et al., "Radiotherapy plus Concomitant and Adjuvant Temozolomide for Glioblastoma," N Engl J Med, vol. 352, pp. 987-996, (2005).
Stupp, R. et al., Supplmentary Appendix to: "Radiotherapy plus Concomitant and Adjuvant Temozolomide for Glioblastoma," N Engl J Med, vol. 352, pp. 987-996, (2005), 4 pages, retrieved on Aug. 6, 2020, from: https://www.nejm.org/doi/suppl/10.1056/NEJMoa043330/suppl_file/987sa1.pdf.
Stupp, R. et al., "Effects of Radiotherapy with Concomitant and Adjuvant Temozolomide Versus Radiotherapy Alone on Survival in Gliobalstoma in a Randomised Phase III Study: 5-year Analysis of the EORTC-NCIC Trial," Lancet Oncol, vol. 10, pp. 459-466, (2009).
Wagner, P. et al., "Effects of Crocetin on Pulmonary Gas Exchange in Foxhounds During Hypoxic Exercise," J Appl Physiol, vol. 89, pp. 235-241, (2000).
Wang, Y. et al., "Perihematomal Cellular Injury Is Reduced by Trans-Sodium Crocetinate in a Model of Intracerebral Hemorrhage," Molecular Neurobiology, vol. 52, pp. 985-989, (2015).
Wang, Y. et al., "Trans-Sodium Crocetinate Improves Outcomes in Rodent Models of Occlusive and Hemorrhagic Stroke," NIH Public Access, Author Manuscript, available in PMC 2015, 18 pages, doi: 10.1016/j.brainres.2014.08.013, face of article states: Published in final edited form as: *Brain Res*. Oct. 2, 2014; 1583: 245-254.

* cited by examiner (Saline Control is the left bar in each pair, and TSC High Dose is the right bar in each pair, in the figure above.)

(Saline Control is the left bar in each pair, and TSC High Dose is the right bar in each pair, in the figure above.)

(Saline Control is the left bar in each pair, and TSC high dose is the right bar in each pair, in the figure above.)

(Control is the far left bar in each group, followed by the bar for TSC with Gem., followed by the bar for TSC 1 hr before Gem., followed by the far right bar for TSC 2 hrs before Gem., in the figure above.)

(Control is the left bar in each pair, and High Dose TSC is the right bar in each pair, in the figure above.)

(Control is the left bar in each pair, and High Dose TSC is the right bar in each pair, in the figure above.)

(Control is the left bar in each pair, and High Dose TSC is the right bar in each pair, in the figure above.)

USE OF BIPOLAR TRANS CAROTENOIDS WITH CHEMOTHERAPY AND RADIOTHERAPY FOR TREATMENT OF CANCER

CROSS-REFERENCE TO RELATED APPLICATIONS

This application is a U.S. National Stage application of International Application No. PCT/US2017/023844, filed Mar. 23, 2017, which claims the benefit of and priority to U.S. Provisional Application No. 62/312,988, filed Mar. 24, 2016, the contents of each of which are incorporated by reference in their entirety.

The subject disclosure relates to the use of bipolar trans carotenoids with chemotherapy and/or radiotherapy for the treatment of cancer including brain and pancreatic cancer.

BACKGROUND

Getting an adequate supply of oxygen to the tissues in our body begins in the lungs, where gas exchange occurs and oxygen enters the bloodstream while carbon dioxide exits the bloodstream to be exhaled. The process of gas exchange occurs via diffusion, which is the movement of molecules from an area of high concentration to an area of low concentration. Once the oxygen enters into the bloodstream it must diffuse through the plasma and then enter red blood cells where it binds to hemoglobin. The oxygen is then transported through the bloodstream, and as it enters areas of the body with low oxygen concentration, the oxygen is off-loaded by the red blood cells so that it can again diffuse through the blood plasma and capillary walls to enter tissues. The oxygen then enters the mitochondria where it is utilized for metabolic purposes.

Each of the steps described above for the movement of oxygen through the body results in some form of resistance, with diffusion through the plasma being a de facto "rate-limiting" step in the movement of oxygen through the body, accounting for 70-90% of the overall resistance. Thus, if the movement of oxygen through plasma could be increased, it would be possible to increase the amount of oxygen that can make its way through the pathway at any given time and into the various tissues in the body, including hypoxic tissues such as tumors.

The process of diffusion follows Fick's law, which states that the rate of oxygen diffusion through plasma is dependent upon 1) the plasma thickness; 2) the concentration gradient of oxygen; and 3) a proportionality constant known as the diffusion coefficient (also known as diffusivity). Thus, those are the three factors that could potentially be altered in order to increase the diffusion of oxygen.

The plasma thickness is set by arterial anatomy, and thus is not readily altered. The concentration gradient of oxygen can be altered by increasing the percentage of oxygen that a patient breathes (air is 21% oxygen) or through the addition of hemoglobin-like molecules into the bloodstream.

It is believed that trans sodium crocetinate (TSC) and other bipolar trans carotenoids alter the molecular arrangement of water molecules in the plasma (which is composed of 90% water), with the altered structure being less dense than untreated plasma. Water is composed of two hydrogen atoms and one oxygen atom, with a net positive charge found on the hydrogen atoms and a net negative charge found on the oxygen atom. This results in the formation of hydrogen bonds, which are simply an attraction between the net-negatively charged oxygen of one water molecule and the net-positively charged hydrogen atoms of another water molecule. Theoretically, one water molecule can form four hydrogen bonds with neighboring water molecules. However, the literature indicates that a water molecule actually forms, on average, 2 to 3.6 hydrogen bonds.

Tumor Hypoxia

Hypoxia is a deficiency in a sufficient supply of oxygen. It has been known for well over 50 years that tumors are specifically susceptible to developing hypoxia, which is driven by a combination of rapid growth, structural abnormalities of the tumor microvessels, and disturbed circulation within the tumor. There are a number of consequences to tumor hypoxia, including:
  Increased resistance to ionizing radiation
  A more clinically aggressive phenotype
  An increased potential for more invasive growth
  Increased regional and distal tumor spreading

Trans Sodium Crocetinate Increases Oxygenation of Hypoxic Tumors

While first studied for the treatment of hemorrhagic shock and ischemia, the use of TSC as an agent to increase the oxygenation of tumors has also been studied. Tumor hypoxia is a leading cause of resistance to both radiation and chemotherapy in a number of solid tumors.

Glioblastoma Multiforme

Glioblastoma multiforme (GBM) is a grade IV brain tumor characterized by a heterogeneous cell population with a number of negative attributes. GBM cells are typically genetically unstable (thus prone to mutation), highly infiltrative, angiogenic, and resistant to chemotherapy. The mutations typically found in GBM allow the tumor to grow and thrive in a hypoxic environment. Both activating mutations and loss of tumor suppressor genes give rise to the highly complex and difficult to treat nature of the disease. For example, approximately 50% of GBM tumors have amplification of the epidermal growth factor receptor (EGFR), which can then induce activation of the PI3K signaling pathway.

GBM is classified into two major subclasses (primary or secondary) depending upon the clinical properties as well as the chromosomal and genetic alterations that are unique to each class. Primary GBM arises de novo from normal glial cells and typically occurs in those over the age of 40, while secondary GBM arises from transformation of lower grade tumors and is usually seen in younger patients). Primary GBM is believed to account for approximately 95% of all GBMs.

While GBM is the most common form of primary brain tumor involving glial cells, it is still relatively rare as approximately 24,000 people in the United States were diagnosed with some form of malignant brain cancer in 2014. Gliomas account for approximately 80% of malignant brain cancers, with GBM accounting for approximately 45% of gliomas. The median age of GBM diagnosis is approximately 65 years, with the incidence of GBM in those over 65 increasing rapidly as shown by a doubling in incidence from 5.1 per 100,000 in the 1970's to 10.6 per 100,000 in the 1990's. Those diagnosed with the disease have a very grim prognosis, with the median survival time of untreated patients being only 4.5 months. Current standard of care treatment only provides 12-14 months of survival time after diagnosis.

Current Treatments for GBM

Standard of care for GBM tumors always begins with surgical resection of the tumor, unless the tumor is deemed inoperable due to its location near vital centers of the brain. This is performed both to alleviate the symptoms associated with the disease as well as to facilitate treatment of any residual tumor cells. Even with advances in surgical technique, complete removal of the tumor with clean margins is almost never possible, as the tumors are highly infiltrative and typically extend into the normal brain parenchyma. Due to this, almost all GBM patients have recurrence of the tumor, with 90% occurring at the primary site.

Due to the invasive nature of the tumors, surgical resection is followed by radiotherapy coupled with the use of chemotherapeutic agents. Radiotherapy involves the administration of irradiation to the whole brain. While nitrosoureas were the most common chemotherapeutic agents used for a number of decades, in 1999 temozolomide (TMZ) became available and is now a part of the standard of care. This is due to a clinical trial that showed the addition of TMZ to surgery and radiation increased median survival in newly diagnosed GBM patients to 14.6 months compared to 12.1 months for the surgery and radiation only group.

Most chemotherapeutic drugs have a limited ability to cross the blood brain barrier (BBB), thus a strategy to circumvent this was the development of dissolvable chemotherapy wafers (Gliadel®) that could be placed in the tumor bed following surgical resection. Gliadel® contains the nitrosourea chemotherapeutic agent carmustine that is released for several weeks, in contrast to systemically administered carmustine that has a very short half-life. While Gliadel® wafers were shown to be safe, the drugs' addition to radiation and TMZ did not result in a statistically significant increase in survival.

GBM tumors show increased expression of VEGF, and bevacizumab has been approved by the FDA for the treatment of recurrent GBM. A Phase 2 study found that bevacizumab treatment in patients with recurrent GBM increased six-month progression-free survival from a historical 9-15% to 25% with overall six-month survival of 54%. Another Phase 2 study showed that recurrent GBM patients treated with bevacizumab at a lower dose but a higher frequency had even higher six-month progression-free survival of 42.6%.

While bevacizumab has shown success in recurrent GBM, it is not utilized in newly diagnosed patients as two separate clinical trials showed no difference in overall survival in patients treated with radiation, TMZ, and bevacizumab compared to patients treated with only radiation and TMZ. Bevacizumab treatment did result in an increase in progression free survival in both studies; however, why the effect in progression free survival did not translate to an increase in overall survival is unclear. In addition, it was reported that patients treated with bevacizumab had an increased symptom burden, a worse quality of life, and a decline in neurocognitive function.

Pancreatic Cancer

It is estimated that in 2016 approximately 49,000 people will be diagnosed with pancreatic cancer in the United States. More than half of these patients will be diagnosed with metastatic disease. The five-year survival rates for patients with pancreatic cancer are dismal (<14%) and are particularly bad for those with metastatic disease (~1%).

Pancreatic cancer is responsible for 7% of all cancer deaths in both men and women, making it the fourth leading cause of cancer death in the U.S. Estimates indicate that 40% of pancreatic cancer cases are sporadic in nature, 30% are related to smoking, 20% may be associated with dietary factors, with only 5-10% hereditary.

Pancreatic cancer is difficult to diagnose in early stages. The reason for this is because initial symptoms of the disease are often nonspecific and subtle in nature, and include anorexia, malaise, nausea, fatigue, and back pain. Approximately 75% of all pancreatic carcinomas occur within the head or neck of the pancreas, 15-20% occur in the body of the pancreas, and 5-10% occur in the tail.

The only potential curative therapy for pancreatic cancer is complete surgical resection. Unfortunately, this is only possible for approximately 20% of cases, and even of those patients whose cancer is surgically resected, 80% will develop metastatic disease within two to three years following surgery. Patients with unresectable pancreatic cancer have a median overall survival of 10 to 14 months while patients diagnosed with Stage IV disease (indicative of metastases) have a 5-year overall survival of just 1%.

Pancreatic cancers are highly hypoxic as shown by the results of multiple studies. A study reporting the direct measurement of oxygenation in human pancreatic tumors prior to surgery showed dramatic differences between tumors and normal tissue. The partial pressure of oxygen (pO2) ranged between 0-5.3 mmHg in tumors but in adjacent normal tissue it ranged from 9.3-92.7 mmHg. Hypoxic areas are also frequently found when examining tissue from mouse models of pancreatic cancer.

The exocrine cells and endocrine cells of the pancreas form different types of tumors. It's very important to distinguish between exocrine and endocrine cancers of the pancreas. They have distinct risk factors and causes, have different signs and symptoms, are diagnosed using different tests, are treated in different ways, and have different outlooks.

Exocrine Tumors

Exocrine tumors are by far the most common type of pancreas cancer. When someone says that they have pancreatic cancer, they usually mean an exocrine pancreatic cancer.

Pancreatic Adenocarcinoma

An adenocarcinoma is a cancer that starts in gland cells. About 95% of cancers of the exocrine pancreas are adenocarcinomas. These cancers usually begin in the ducts of the pancreas. But sometimes they develop from the cells that make the pancreatic enzymes, in which case they are called acinar cell carcinomas.

Less Common Types of Cancers

Other cancers of the exocrine pancreas include adenosquamous carcinomas, squamous cell carcinomas, signet ring cell carcinomas, undifferentiated carcinomas, and undifferentiated carcinomas with giant cells. These types are distinguished from one another based on how they look under the microscope.

Solid Pseudopapillary Noplasms (SPNs)

These are rare, slow-growing tumors that almost always occur in young women. Even though these tumors tend to grow slowly, they can sometimes spread to other parts of the body, so they are best treated with surgery. The outlook for people with these tumors is usually very good.

Ampullary Cancer (Carcinoma of the Ampulla of Vater)

This cancer starts in the ampulla of Vater, which is where the bile duct and pancreatic duct come together and empty into the small intestine. Ampullary cancers aren't technically pancreatic cancers, but they are included in this document because their treatments are very similar.

Ampullary cancers often block the bile duct while they are still small and have not spread far. This blockage causes bile to build up in the body, which leads to yellowing of the skin and eyes (jaundice) and can turn urine dark. Because of this, these cancers are usually found at an earlier stage than most pancreatic cancers, and they usually have a better prognosis (outlook) than typical pancreatic cancers.

Endocrine Tumors

Tumors of the endocrine pancreas are uncommon, making up less than 4% of all pancreatic cancers. As a group, they are sometimes known as pancreatic neuroendocrine tumors (NETs) or islet cell tumors.

Pancreatic NETs can be benign or malignant (cancer). Benign and malignant tumors can look alike under a microscope, so it isn't always clear whether or not a pancreatic NET is cancer. Sometimes the diagnosis only becomes clear when the tumor spreads outside of the pancreas. There are many types of pancreatic NETs.

Functioning Tumors

About half of pancreatic NETs make hormones that are released into the blood and cause symptoms. These are called functioning tumors. Each one is named for the type of hormone-making cell it starts in.

Gastrinomas come from cells that make gastrin. About half of gastrinomas are cancers.

Insulinomas come from cells that make insulin. Most insulinomas are benign (not cancers).

Glucagonomas come from cells that make glucagon. Most glucagonomas are cancers.

Somatostatinomas come from cells that make somatostatin. Most somatostatinomas are cancers.

VIPomas come from cells that make vasoactive intestinal peptide (VIP). Most VIPomas are cancers.

PPomas come from cells that make pancreatic polypeptide. Most PPomas are cancers.

The most common types of functioning NETs are gastrinomas and insulinomas. The other types occur very rarely.

Non-Functioning Tumors

These tumors don't make enough excess hormones to cause symptoms. They are more likely to be cancer than functioning tumors. Because they don't make excess hormones that cause symptoms, they can often grow quite large before they are found.

Carcinoid Tumors

These are another type of NET that rarely can start in the pancreas, although they are much more common in other parts of the digestive system. These tumors often make serotonin (also called 5-HT) or its precursor, 5-HTP.

The treatment and outlook for pancreatic NETs depend on the specific tumor type and the stage (extent) of the tumor, but the outlook is generally better than that of pancreatic exocrine cancers.

Current Treatment Options for Pancreatic Cancer

Surgery remains the primary mode of treatment for patients with pancreatic cancer. However, there is an important role for chemotherapy and/or radiation in an adjuvant (given to prevent recurrence) or neoadjuvant (given before surgery to shrink the tumor to make complete resection more probable) setting as well as in patients with unresectable disease.

Since its approval in 1996, gemcitabine has been partnered with approximately 30 different agents in late-stage clinical trials in an attempt to improve upon the effectiveness of gemcitabine alone in treating patients with metastatic pancreatic cancer. Only two of these trials have led to an FDA approval—erlotinib (Tarceva®) and nab-paclitaxel (Abraxane®).

In patients with metastatic disease, the use of erlotinib with gemcitabine led to a significantly higher one-year survival rate than with the use of gemcitabine alone (23% vs. 17%, $P=0.023$) as well as an increased median overall survival (6.24 months vs. 5.91 months, $P=0.038$). A more recent study showed that the addition of nanoparticle albumin-bound (nab)-paclitaxel to gemcitabine significantly improved overall survival in treatment naïve patients with metastatic cancer, as overall survival was approximately two months longer in patients treated with combination therapy (8.5 vs. 6.7 months).

The Folfirinox (leucovorin+5-fluorouracil+oxaliplatin+irinotecan) regimen was shown to significantly improve overall survival compared to treatment with gemcitabine (11.1 months vs. 6.8 months). While dramatically improving overall survival, the Folfirinox treatment was accompanied by serious adverse events and thus is only recommended for patients with good performance status.

Other combinations of gemcitabine with cisplatin, oxaliplatin, irinotecan, or docetaxel tested in Phase 3 trials have not been of superior benefit to gemcitabine alone. The combination therapy nab-paclitaxel and gemcitabine was recently approved by the FDA as an additional standard of care for the treatment of patients with untreated pancreatic adenocarcinoma. However, the improvements were modest, and treatment of pancreatic cancer remains an intense area of research, with 92 products in all stages of clinical development with 14 of them in Phase 3 at this time according to clinicaltrials.gov.

Just recently, the FDA approved Onivyde® (irinotecan liposome injection) in combination with fluorouracil and leucovorin, to treat patients with metastatic pancreatic cancer who were previously treated with gemcitabine-based chemotherapy. In the pivotal clinical trial, patients treated with Onivyde® plus fluorouracil/leucovorin lived an average of 6.1 months, compared to 4.2 months for those treated with only fluorouracil/leucovorin.

Brain Metastases

In contrast to the relative rarity of primary brain cancers, life-threatening cancers that metastasize to the brain are much more common and represent a serious complication in the treatment of many cancer types. Up to 30% of adult cancer patients will suffer from brain metastases. There are approximately 170,000 cases of metastatic brain cancer every year in the United States. Incidence of brain metastases varies depending upon the primary tumor type, although lung cancer appears to carry the greatest risk. The prognosis for patients with brain metastases is very grim, with current treatment options only resulting in median overall survival times of less than one year.

Treatment for brain metastases involves both controlling the symptoms associated with the condition as well as attacking cancer directly. Brain metastases typically result in edema that can be controlled with the use of steroids; however, long-term use of steroids typically results in side effects that greatly diminishes a patient's quality of life. Approximately 25-45% of patients will experience seizures and require the use anti-epileptic drugs. Surgery is only utilized in patients with a solitary brain metastatic lesion. Radiation therapy remains the standard of care for the vast majority of patients with brain metastases. There is very limited evidence for the use of chemotherapy, as few clinical trials have been conducted. There are no medications approved for the treatment of brain metastases.

Chemotherapy

Chemotherapy drugs can be grouped by how they work, their chemical structure, and their relationships to other drugs. Some drugs work in more than one way, and may belong to more than one group. Knowing how the drug works is important in predicting side effects from it. This helps doctors decide which drugs are likely to work well together. If more than one drug will be used, this information also helps them plan exactly when each of the drugs should be given (in which order and how often).

Alkylating Agents

Alkylating agents keep the cell from reproducing by damaging its DNA. These drugs work in all phases of the cell cycle and are used to treat many different cancers, including cancers of the lung, breast, and ovary as well as leukemia, lymphoma, Hodgkin disease, multiple myeloma, and sarcoma.

Because these drugs damage DNA, they can affect the cells of the bone marrow which make new blood cells. In rare cases, this can lead to leukemia. The risk of leukemia from alkylating agents is "dose-dependent," meaning that the risk is small with lower doses, but goes up as the total amount of the drug used gets higher. The risk of leukemia after getting alkylating agents is highest about 5 to 10 years after treatment.

Antimetabolites

Antimetabolites interfere with DNA and RNA growth by substituting for the normal building blocks of RNA and DNA. These agents damage cells during the phase when the cell's chromosomes are being copied. They are commonly used to treat leukemias, cancers of the breast, ovary, and the intestinal tract, as well as other types of cancer.

Anti-Tumor Antibiotics

These drugs are not like the antibiotics used to treat infections. They work by changing the DNA inside cancer cells to keep them from growing and multiplying.

Topoisomerase Inhibitors

These drugs interfere with enzymes called topoisomerases, which help separate the strands of DNA so they can be copied. (Enzymes are proteins that cause chemical reactions in living cells.) Topoisomerase inhibitors are used to treat certain leukemias, as well as lung, ovarian, gastrointestinal, and other cancers.

Topoisomerase II inhibitors can increase the risk of a second cancer—acute myelogenous leukemia (AML)—as early as 2 to 3 years after the drug is given.

Mitotic Inhibitors

Mitotic inhibitors are compounds derived from natural products, such as plants. They work by stopping cells from dividing to form new cells but can damage cells in all phases by keeping enzymes from making proteins needed for cell reproduction. They are used to treat many different types of cancer including breast, lung, myelomas, lymphomas, and leukemias. These drugs may cause nerve damage, which can limit the amount that can be given.

Other Chemotherapy Drugs

Some chemotherapy drugs act in slightly different ways and do not fit well into any of the other categories. Examples include drugs like L-asparaginase, which is an enzyme, and the proteosome inhibitor bortezomib (Velcade®).

U.S. Pat. No. 8,030,350 discloses the use of bipolar trans carotenoids along with chemotherapy and radiation therapy for the treatment of cancer.

SUMMARY

In one embodiment, the disclosure includes a method of treating cancer (solid tumor) in a mammal (e.g. human) comprising
a) administering to the mammal a bipolar trans carotenoid salt having the formula:

where:
Y=a cation which can be the same or different,
Z=a polar group which can be the same or different and which is associated with the cation, and
TCRO=a linear trans carotenoid skeleton with conjugated carbon-carbon double bonds and single bonds, and having pendant groups X, wherein the pendant groups X, which can be the same or different, are a linear or branched hydrocarbon group having 10 or less carbon atoms, or a halogen,
b) administering to the mammal radiation therapy, wherein said bipolar trans carotenoid salt is administered at time and at a dose causing increased partial pressure of oxygen in the tumor during administration of said radiation.

In a preferred embodiment, the bipolar trans carotenoid is TSC administered at a dose of 0.15-0.35 mg/kg 45-60 minutes prior to administration of said radiation therapy. In some embodiments, the subject mammal is also administered chemotherapy in addition to the radiation therapy, e.g. administering temozolomide 7 times per week for 6 weeks.

A still further embodiment of the disclosure relates to a method of treating cancer (solid tumor) in a mammal (e.g. human) comprising a) administering to the mammal a bipolar trans carotenoid salt having the formula:

YZ-TCRO-ZY where:
Y=a cation which can be the same or different,
Z=a polar group which can be the same or different and which is associated with the cation, and
TCRO=a linear trans carotenoid skeleton with conjugated carbon-carbon double bonds and single bonds, and having pendant groups X, wherein the pendant groups X, which can be the same or different, are a linear or branched hydrocarbon group having 10 or less carbon atoms, or a halogen,
b) administering chemotherapy to the mammal, wherein said bipolar trans carotenoid salt is administered at a time and at a dose causing increased partial pressure of oxygen in the tumor during administration of said chemotherapy.

In a preferred embodiment, TSC administered at a dose of 0.75-2.0 mg/kg 1-2 hour prior to administration of said chemotherapy.

The cancer is selected from the group consisting of squamous cell carcinomas, melanomas, lymphomas, sarcomas, sarcoids, osteosarcomas, skin cancer, breast cancer, head and neck cancer, gynecological cancer, urological and male genital cancer, bladder cancer, prostate cancer, bone cancer, cancers of the endocrine glands (e.g. pancreatic cancer), cancers of the alimentary canal, cancers of the major digestive glands/organs, CNS cancer, and lung cancer. The chemotherapy is selected from the group consisting of alkylating agents, antimetabolites, antitumor antibiotics, topoisomerase inhibitors, and anti-microtubule agents. In some embodiments, the subject mammal is also administered radiation therapy in addition to the chemotherapy.

In an advantageous embodiment, the bipolar trans carotenoid is TSC administered at a dose of 0.75-2.0 mg/kg, 1-2 hrs. prior to administration of said chemotherapy. The chemotherapy is one or more compounds selected from the group consisting of gemcitabine, 5-fluorouracil (5-FU), irinotecan, oxaliplatin, nab-paclitaxel (albumin-bound paclitaxel), capecitabine, cisplatin, elotinib, paclitaxel, docetaxel, and irinotecan liposome.

In one embodiment, the method is administering 1.5 mg/kg TSC 45-60 minutes prior administering the chemotherapy, and administering the chemotherapy is administering gemcitabine as an IV infusion once per week for 3 weeks followed by a week of rest.

In another embodiment, 1.5 mg/kg TSC is administered 45-60 minutes prior administering the chemotherapy, and administering the chemotherapy is administering nab-paclitaxel as an IV infusion followed by gemcitabine as an IV infusion, once per week for 3 weeks followed by a week of rest.

In another embodiment, the subject disclosure relates to a method of treating a cancer of the pancreas in a mammal (e.g. human) comprising:
a) administering to the mammal a bipolar trans carotenoid salt having the formula:

YZ-TCRO-ZY where:
Y=a cation which can be the same or different,
Z=a polar group which can be the same or different and which is associated with the cation, and
TCRO=a linear trans carotenoid skeleton with conjugated carbon-carbon double bonds and single bonds, and having pendant groups X, wherein the pendant groups X, which can be the same or different, are a linear or branched hydrocarbon group having 10 or less carbon atoms, or a halogen, and
b) administering to the mammal chemotherapy, wherein the bipolar trans carotenoid salt is administered at a time and at a dose causing increased partial pressure of oxygen in the tumor during administration of the chemotherapy.

In an advantageous embodiment, the bipolar trans carotenoid is TSC administered at a dose of 0.75-2.0 mg/kg, 1-2 hrs. prior to administration of said chemotherapy. The chemotherapy is one or more compounds selected from the group consisting of gemcitabine, 5-fluorouracil (5-FU), irinotecan, oxaliplatin, nab-paclitaxel (albumin-bound paclitaxel), capecitabine, cisplatin, elotinib, paclitaxel, docetaxel, and irinotecan liposome.

In one embodiment, the method is administering 1.5 mg/kg TSC 45-60 minutes prior administering the chemotherapy, and administering the chemotherapy is administering gemcitabine as an IV infusion once per week for 3 weeks followed by a week of rest.

In another embodiment, 1.5 mg/kg TSC is administered 45-60 minutes prior administering the chemotherapy, and administering the chemotherapy is administering nab-paclitaxel as an IV infusion followed by gemcitabine as an IV infusion, once per week for 3 weeks followed by a week of rest.

The disclosure also relates to a method of treating a cancer of the brain (e.g. glioblastoma) in a mammal (e.g. human) comprising:
a) administering to the mammal a bipolar trans carotenoid salt having the formula:

YZ-TCRO-ZY where:
Y=a cation which can be the same or different,
Z=a polar group which can be the same or different and which is associated with the cation, and
TCRO=a linear trans carotenoid skeleton with conjugated carbon-carbon double bonds and single bonds, and having pendant groups X, wherein the pendant groups X, which can be the same or different, are a linear or branched hydrocarbon group having 10 or less carbon atoms, or a halogen, and
b) administering radiation therapy to the mammal wherein the bipolar trans carotenoid salt is administered at time and at a dose causing increased partial pressure of oxygen in the tumor during administration of said radiation.

When the bipolar trans carotenoid is TSC, it is administered at a dose of 0.15-0.35 mg/kg 45-60 minutes prior to said administration, typically external beam radiation therapy. In one embodiment, the radiation therapy is administering 5 times per week for 6 weeks. In another embodiment, the method includes administering chemotherapy to the mammal, e.g. administering temozolomide 7 times per week for 6 weeks.

In all of the above embodiments, advantageously the bipolar trans carotenoid salt is TSC is in the form of a composition with a cyclodextrin.

BRIEF DESCRIPTION OF THE FIGURES

Certain aspects of the disclosure will be apparent with regard to the following figures.

DETAILED DESCRIPTION

The subject disclosure relates to compounds and compositions including chemotherapy agents and bipolar trans carotenoids, and the use of such compounds for the treatment of various cancers including pancreatic and brain cancers.

It is well established that tumors are hypoxic with many tumor types being highly hypoxic. See Table 1 below:

TABLE 1

Oxygenation of tumors and the surrounding normal tissue (aggregated from multiple studies)

| Tumor Type | Median Tumor pO$_2$* (number of patients) | Median Normal pO$_2$* (number of patients) |
|---|---|---|
| Glioblastoma | 4.9 (10) | ND |
|  | 5.6 (14) | ND |
| Head and Neck | 12.2 (30) | 40.0 (14) |
| Carcinoma | 14.7 (23) | 43.8 (30 |
|  | 14.6 (65) | 51.2 (65) |
| Lung Cancer | 7.5 (17) | 38.5 (17) |
| Breast Cancer | 10.0 (15) | ND |
| Pancreatic Cancer | 2.7 (7) | 51.6 (7) |
| Cervical Cancer | 5.0 (8) | 51 (8) |
|  | 5.0 (74) | ND |
|  | 3.0 (86) | ND |
| Prostate Cancer | 2.4 (59) | 30.0 (59) |
| Soft Tissue Sarcoma | 6.2 (34) | ND5 |
|  | 18 (22) | ND |

*pO2 measured in mmHg. Measurements were made using a commercially available oxygen electrode (the 'Eppendorf' electode). The values shown are the median of the median values for each patient.
ND, not determined; pO2, oxygen partial pressure.
Brown, JM and Wilson, WR. "Exploiting tumour hypoxia in cancer treatment." *Nat. Rev. Cancer* 4(6) 2004: 437-447.

Further, it is known that hypoxic tumors are more resistant to radiotherapy and chemotherapy.

Figure 1:
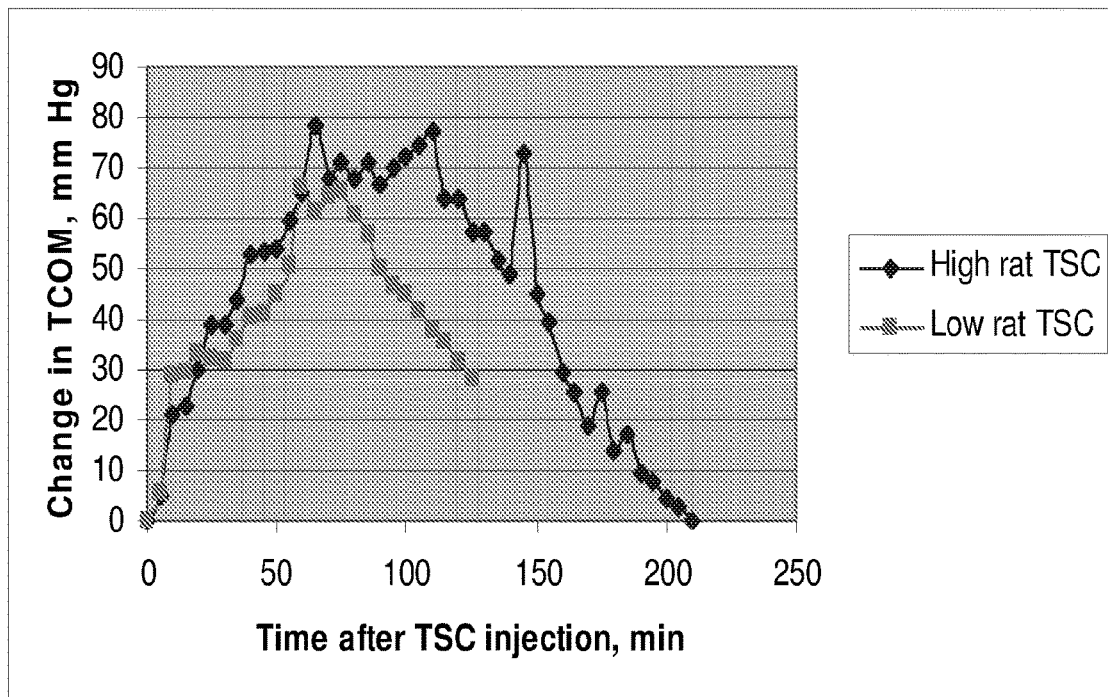
FIG. 1 illustrates the change in partial pressure of oxygen of a hyperoxic rat resulting from administration of a low efficacious dose amount compared to a high efficacious dose amount of TSC.

It has been discovered that for a mammal, there are two concentrations of a bipolar trans carotenoid, such as TSC, that result in increased oxygen partial pressure in a tumor. For humans, the low dose range is 0.15-0.35 mg/kg and the high dose range is 0.75 to 2.0 mg/kg. Both doses result in approximately the same maximum increase in oxygen partial pressure. Importantly, the high dose results in a sustained maximum oxygen partial pressure while the low dose does not. An example of this phenomenon is shown in FIG. 1

The methods of the subject disclosure are directed to administering a dose of a bipolar trans carotenoid at a dose and at the proper time prior to administration of chemotherapy or radiation therapy such that the oxygen partial pressure is elevated inside the tumor while the chemotherapy or radiation therapy is administered so as to obtain increased killing effect of the chemotherapy and or radiotherapy on the cancer cells/tumor.

In one embodiment, provided is a method (Method A) of treating cancer in a mammal (e.g. human) comprising
 a) administering to the mammal a bipolar trans carotenoid salt having the formula:

where:
   Y=a cation which can be the same or different,
   Z=a polar group which can be the same or different and which is associated with the cation, and
   TCRO=a linear trans carotenoid skeleton with conjugated carbon-carbon double bonds and single bonds, and having pendant groups X, wherein the pendant groups X, which can be the same or different, are a linear or branched hydrocarbon group having 10 or less carbon atoms, or a halogen,
 b) administering to the mammal radiation therapy, wherein said bipolar trans carotenoid salt is administered at time and at a dose causing increased partial pressure of oxygen in the tumor during administration of said radiation.

Further provided is Method A as follows:
A.1 Method A, wherein the bipolar trans carotenoid is TSC.
A.2 Method A or A.1, wherein the bipolar trans carotenoid is administered at a dose of 0.05-0.5 mg/kg.
A.3 Method A or A.1-A.2, wherein the bipolar trans carotenoid is administered at a dose of 0.15-0.35 mg/kg.
A.4 Method A or A.1-A.3, wherein the bipolar trans carotenoid is administered at a dose of 0.25 mg/kg.
A.5 Method A or A.1-A.4, wherein the bipolar trans carotenoid is administered 30-120 minutes prior to administration of said radiation therapy.
A.6 Method A or A.1-A.5, wherein the bipolar trans carotenoid is administered 45-60 minutes prior to administration of said radiation therapy.
A.7 Method A of A.1-A.6, wherein the bipolar trans carotenoid is administered 2-5 times per week.
A.8 Method A of A.1-A.7, wherein the bipolar trans carotenoid is administered 3 times per week.
A.9 Method A or A.1-A.8, wherein said radiation therapy is external beam radiation therapy (e.g., three-dimensional conformal radiation therapy, intensity modulated radiation therapy, proton beam therapy, stereotactic radiation therapy).
A.10 Method A or A.1-A.8, wherein said radiation therapy is internal beam radiation therapy.
A.11 Method A or A.1-A.10, wherein said radiation therapy is administered in an amount between 0.1 Gy and 5 Gy per radiation therapy session.
A.12 Method A or A.1-A.11, wherein said radiation therapy is administered in an amount of 2 Gy per radiation therapy session.
A.13 Method A or A.1-A.12, wherein said radiation therapy is administered 5 times per week for 6 weeks.

A.14 Method A or A.1-A.13, further comprising administering chemotherapy to said mammal.

A.15 Method A.14, wherein the chemotherapy is administered at least once a week for at least three weeks.

A.16 Method A.14 or A.15, wherein the chemotherapy is administered 7 times a week for 6 weeks.

A.17 Any of Methods A.14-A.16, wherein said chemotherapy is selected from the group consisting of alkylating agents, antimetabolites, antitumor antibiotics, topoisomerase inhibitors, and anti-microtubule agents.

A.18 Any of Methods A.14-A.17, wherein said chemotherapy is one or more compounds selected from the group consisting of temozolomide, gemcitabine, 5-fluorouracil (5-FU), irinotecan, oxaliplatin, nab-paclitaxel (albumin-bound paclitaxel), capecitabine, cisplatin, elotinib, paclitaxel, docetaxel, and irinotecan liposome.

A.19 Any of Methods A.14-A.18, wherein said chemotherapy is one or more compounds selected from temozolomide, gemcitabine, irinotecan, and celecoxib.

A.20 Any of Methods A.14-A.19, wherein said chemotherapy is one or both of gemcitabine and nab-paclitaxel.

A.21 Any of Methods A.14-A.20, wherein said chemotherapy is gemcitabine.

A.22 Any of Methods A.14-A.21, wherein said chemotherapy is temozolomide.

A.23 Any of Methods A.14-A.22 or A.22, wherein said administering chemotherapy comprises administering temozolomide 7 times per week for 6 weeks.

A.24 Any of Methods A.14-A.23, wherein said chemotherapy is administered after said radiation therapy.

A.25 Any of Methods A.14-A.24, wherein said bipolar trans carotenoid salt is administered with chemotherapy at a dose of 1.5 mg/kg.

A.26 Method A or A.1-A.25, wherein said cancer is brain cancer.

A.27 Method A or A.1-A.26, wherein said brain cancer is a glioblastoma multiforme.

A.28 Method A or A.1-A.27, wherein the bipolar trans carotenoid salt is TSC is in the form of a composition with a cyclodextrin.

A.29 Method A or A.1-A.28, wherein the bipolar trans carotenoid salt is TSC is in the form of a lyophilized composition with a cyclodextrin.

A.30 Method A or A.1-A.29, wherein the bipolar trans carotenoid is synthetic TSC.

A.31 Method A or A.1-A.30, wherein the absorbency of the bipolar trans carotenoid salt (i.e., TSC) at a highest peak occurring in the visible light wavelength range (i.e., between 380 to 470 nm) divided by the absorbency of a peak occurring in the ultraviolet wavelength range (i.e., between 220 to 300 nm) is greater than 7, greater than 7.5, greater than 8.0, or greater than 8.5.

A.32 Method A.31, wherein the quotient obtained is between 7.5 and 9.0.

A.33 Method A.32, wherein the quotient obtained is between 8.0 and 8.8.

In another embodiment, provided is a method (Method B) of treating cancer in a mammal (e.g. human) comprising a) administering to the mammal a bipolar trans carotenoid salt having the formula:

YZ-TCRO-ZY where:
Y=a cation which can be the same or different,
Z=a polar group which can be the same or different and which is associated with the cation, and TCRO=a linear trans carotenoid skeleton with conjugated carbon-carbon double bonds and single bonds, and having pendant groups X, wherein the pendant groups X, which can be the same or different, are a linear or branched hydrocarbon group having 10 or less carbon atoms, or a halogen, b) administering chemotherapy to the mammal, wherein said bipolar trans carotenoid salt is administered at a time and at a dose causing increased partial pressure of oxygen in the tumor during administration of said chemotherapy.

Further provided is Method B as follows:

B.1 Method B, wherein the bipolar trans carotenoid is TSC.

B.2 Method B or B.1, wherein said bipolar trans carotenoid is administered at a dose of 0.6-2.5 mg/kg.

B.3 Method B or B.1-B.2, wherein said bipolar trans carotenoid is administered at a dose of 0.75-2.0 mg/kg.

B.4 Method B or B.1-B.3, wherein said bipolar trans carotenoid is administered at a dose of 1.5 mg/kg.

B.5 Method B or B.1-B.4, wherein the bipolar trans carotenoid is administered 30-120 minutes prior to administration of said chemotherapy.

B.6 Method B or B.1-B.5, wherein the bipolar trans carotenoid is administered 45-60 minutes prior to administration of said chemotherapy.

B.7 Method B or B.1-B.6, wherein the bipolar trans carotenoid is administered once per week.

B.8 Method B or B.1-B.7, wherein the bipolar trans carotenoid is administered once per week for 3 weeks.

B.9 Method B or B.1-B.8, wherein the chemotherapy is administered at least once a week for at least three weeks.

B.10 Method B or B.1-B.9, wherein the chemotherapy is administered 7 times a week for 6 weeks.

B.11 Method B or B.1-B.10, wherein said chemotherapy is selected from the group consisting of alkylating agents, antimetabolites, antitumor antibiotics, topoisomerase inhibitors, and anti-microtubule agents.

B.12 Method B or B.1-B.11, wherein said chemotherapy is one or more compounds selected from the group consisting of temozolomide, gemcitabine, 5-fluorouracil (5-FU), irinotecan, oxaliplatin, nab-paclitaxel (albumin-bound paclitaxel), capecitabine, cisplatin, elotinib, paclitaxel, docetaxel, and irinotecan liposome.

B.13 Method B or B.1-B.12, wherein said chemotherapy is one or more compounds selected from temozolomide, gemcitabine, irinotecan, and celecoxib.

B.14 Method B or B.1-B.13, wherein said chemotherapy is one or both of gemcitabine and nab-paclitaxel.

B.15 Method B or B.1-B.14, wherein said chemotherapy is gemcitabine.

B.16 Method B or B.1-B.15, wherein said chemotherapy is temozolomide.

B.17 Method B or B.1-B.16, wherein said administering chemotherapy comprises administering temozolomide 7 times per week for 6 weeks.

B.18 Method B or B.1-B.17, wherein administering said bipolar trans carotenoid is administering 1.5 mg/kg TSC 45-60 minutes prior administering said chemotherapy, and administering said chemotherapy is administering gemcitabine as an IV infusion once per week for 3 weeks followed by a week of rest.

B.19 Method B or B.1-B.18, wherein administering said bipolar trans carotenoid is administering 1.5 mg/kg TSC 45-60 minutes prior administering said chemotherapy, and administering said chemotherapy is administering nab-paclitaxel as an IV infusion followed by gemcitabine as an IV infusion, once per week for 3 weeks followed by a week of rest.

B.20 Method B or B.1-B.19, wherein said cancer is a solid tumor.

B.21 Method B or B.1-B.20, wherein the cancer is selected from the group consisting of squamous cell carcinomas, melanomas, lymphomas, sarcomas, sarcoids, osteosarcomas, skin cancer, breast cancer, head and neck cancer, gynecological cancer, urological and male genital cancer, bladder cancer, prostate cancer, bone cancer, cancers of the endocrine glands (e.g., pancreatic cancer), cancers of the alimentary canal, cancers of the major digestive glands/organs, CNS cancer, and lung cancer.

B.22 Method B or B.1-B.21, wherein the cancer is pancreatic cancer.

B.23 Method B or B.1-B.22, wherein the bipolar trans carotenoid salt is TSC is in the form of a lyophilized composition with a cyclodextrin.

B.24 Method B or B.1-B.23, wherein the bipolar trans carotenoid is synthetic TSC.

B.25 Method B or B.1-B.24, wherein the absorbency of the bipolar trans carotenoid salt (i.e., TSC) at a highest peak occurring in the visible light wavelength range (i.e., between 380 to 470 nm) divided by the absorbency of a peak occurring in the ultraviolet wavelength range (i.e., between 220 to 300 nm) is greater than 7, greater than 7.5, greater than 8.0, or greater than 8.5.

B.26 Method B.25, wherein the quotient obtained is between 7.5 and 9.0.

B.27 Method B.26, wherein the quotient obtained is between 8.0 and 8.8.

In another embodiment, provided is a method (Method C) of preventing or treating stroke in a mammal (e.g. human) comprising administering to the mammal a bipolar trans carotenoid salt having the formula:

YZ-TCRO-ZY where:
Y=a cation which can be the same or different,
Z=a polar group which can be the same or different and which is associated with the cation, and
TCRO=a linear trans carotenoid skeleton with conjugated carbon-carbon double bonds and single bonds, and having pendant groups X, wherein the pendant groups X, which can be the same or different, are a linear or branched hydrocarbon group having 10 or less carbon atoms, or a halogen, wherein said bipolar trans carotenoid salt is administered at a dose effective to treat stroke.

Further provided is Method C as follows:

C.1 Method C, wherein the bipolar trans carotenoid is TSC.

C.2 Method C or C.1, wherein the bipolar trans carotenoid is administered at a dose of 0.05-0.5 mg/kg.

C.3 Method C or C.1-C.2, wherein the bipolar trans carotenoid is administered at a dose of 0.15-0.35 mg/kg.

C.4 Method C or C.1-C.3, wherein the bipolar trans carotenoid is administered at a dose of 0.25 mg/kg.

C.5 Method C or C.1-C.4, wherein said stroke is an ischemic stroke or a hemorrhagic stroke.

C.6 Method C or C.1-C.5, wherein said stroke is an ischemic stroke.

C.7 Method C or C.1-C.6, wherein said stroke is a hemorrhagic stroke.

C.8 Method C or C.1-C.7, wherein the bipolar trans carotenoid salt is TSC is in the form of a composition with a cyclodextrin.

C.9 Method C or C.1-C.8, wherein the bipolar trans carotenoid salt is TSC is in the form of a lyophilized composition with a cyclodextrin.

C.10 Method C or C.1-C.9, wherein the bipolar trans carotenoid is synthetic TSC.

C.11 Method C or C.1-C.10, wherein the absorbency of the bipolar trans carotenoid salt (i.e., TSC) at a highest peak occurring in the visible light wavelength range (i.e., between 380 to 470 nm) divided by the absorbency of a peak occurring in the ultraviolet wavelength range (i.e., between 220 to 300 nm) is greater than 7, greater than 7.5, greater than 8.0, or greater than 8.5.

C.12 Method C or C.1-C.11, wherein the quotient obtained is between 7.5 and 9.0.

C.13 Method C or C.1-C.12, wherein the quotient obtained is between 8.0 and 8.8.

In another embodiment, provided is a bipolar trans carotenoid salt (as defined in Method A, B or C) for use in treating cancer in a patient receiving radiation therapy and/or chemotherapy, e.g., for use in a method according to any of Methods A, et seq.; Methods B, et seq.; or Methods C, et seq.

In another embodiment, provided is a use of a bipolar trans carotenoid salt (as defined in Method A, B or C) in the manufacture of a medicament for treating cancer in a patient receiving radiation therapy and/or chemotherapy, e.g., in a method according to any of Methods A, et seq.; Methods B, et seq.; or Methods C, et seq.

In another embodiment, provided is a pharmaceutical composition comprising an effective amount of a bipolar trans carotenoid salt (as defined in Method A, B or C) for use in treating cancer in a patient receiving radiation therapy and/or chemotherapy, e.g., for use in a method according to any of Methods A, et seq.; Methods B, et seq.; or Methods C, et seq.

Compositions

Bipolar Trans Carotenoids

The subject disclosure relates to trans carotenoids including trans carotenoid diesters, dialcohols, diketones and diacids, bipolar trans carotenoids (BTC), and bipolar trans carotenoid salts (BTCS) compounds and synthesis of such compounds having the structure:

YZ-TCRO-ZY where:
Y (which can be the same or different at the two ends)=H or a cation other than H, preferably $Na^+$ or $K^+$ or $Li^+$. Y is advantageously a monovalent metal ion. Y can also be an organic cation, e. g., $R_4N^+$, $R_3S^+$, where R is H, or $C_nH_{2n+1}$ where n is 1-10, advantageously 1-6. For example, R can be methyl, ethyl, propyl or butyl.

Z (which can be the same or different at the two ends)=polar group which is associated with H or the cation. Optionally including the terminal carbon on the carotenoid (or carotenoid related compound), this group can be a carboxyl ($COO^-$) group or a CO group (e.g. ester, aldehyde or ketone group), or a hydroxyl group. This group can also be a sulfate group ($OSO_3^-$) or a monophosphate group ($OPO_3^-$), ($OP(OH)O_2^-$), a diphosphate group, triphosphate or combinations thereof. This group can also be an ester group of COOR where the R is $C_nH_{2n+1}$.

TCRO=trans carotenoid or carotenoid related skeleton (advantageously less than 100 carbons) which is linear, has pendant groups (defined below), and typically comprises "conjugated" or alternating carbon-carbon double and single bonds (in one embodiment, the TCRO is not fully conjugated as in a lycopene). The pendant groups (X) are typically methyl groups but can be other groups as discussed below. In an advantageous embodiment, the units of the skeleton are joined in such a manner that their arrangement is reversed at the center of the molecule. The 4 single bonds that surround a carbon-carbon double bond all lie in the same plane. If the pendant groups are on the same side of the carbon-carbon double bond, the groups are designated as cis (also known as "Z"); if they are on the opposite side of the carbon-carbon bond, they are designated as trans (also known as "E"). Throughout this case, the isomers will be referred to as cis and trans.

The compounds of the subject disclosure are trans. The cis isomer typically is a detriment—and results in the diffusivity not being increased. The placement of the pendant groups can be symmetric relative to the central point of the molecule or can be asymmetric so that the left side of the molecule does not look the same as the right side of the molecule either in terms of the type of pendant group or their spatial relationship with respect to the center carbon.

The pendant groups X (which can be the same or different) are hydrogen (H) atoms, or a linear or branched hydrocarbon group having 10 or less carbons, advantageously 4 or less, (optionally containing a halogen), or a halogen. X could also be an ester group (COO—) or an ethoxy/methoxy group. Examples of X are a methyl group (CH3), an ethyl group (C2H5), a phenyl or single aromatic ring structure with or without pendant groups from the ring, a halogen-containing alkyl group (C1-C10) such as CH2Cl, or a halogen such as Cl or Br or a methoxy (OCH3) or ethoxy (OCH2CH3). The pendant groups can be the same or different but the pendant groups utilized must maintain the skeleton as linear.

Although many carotenoids exist in nature, carotenoid salts do not. Commonly-owned U.S. Pat. No. 6,060,511 hereby incorporated by reference in its entirety, relates to trans sodium crocetinate (TSC). The TSC was made by reacting naturally occurring saffron with sodium hydroxide followed by extractions that selected primarily for the trans isomer.

The presence of the cis and trans isomers of a carotenoid or carotenoid salt can be determined by looking at the ultraviolet-visible spectrum for the carotenoid sample dissolved in an aqueous solution. Given the spectrum, the value of the absorbance of the highest peak which occurs in the visible wave length range of 380 to 470 nm (the number depending on the solvent used and the chain length of the BTC or BTCS. The addition of pendant groups or differing chain lengths will change this peak absorbance but someone skilled in the art will recognize the existence of an absorbance peak in the visible range corresponding to the conjugated backbone structure of these molecules.) is divided by the absorbency of the peak which occurs in the UV wave length range of 220 to 300 nm can be used to determine the purity level of the trans isomer. When the trans carotenoid diester (TCD) or BTCS is dissolved in water, the highest visible wave length range peak will be at between 380 nm to 470 nm (depending on the exact chemical structure, backbone length and pendant groups) and the UV wave length range peak will be between 220 to 300 nm According to M. Craw and C. Lambert, Photochemistry and Photobiology, Vol. 38 (2), 241-243 (1983) hereby incorporated by reference in its entirety, the result of the calculation (in that case crocetin was analyzed) was 3.1, which increased to 6.6 after purification.

Performing the Craw and Lambert analysis, using a cuvette designed for UV and visible wavelength ranges, on the trans sodium salt of crocetin of commonly owned U.S. Pat. No. 6,060,511 (TSC made by reacting naturally occurring saffron with sodium hydroxide followed by extractions which selected primarily for the trans isomer), the value obtained averages about 6.8. Performing that test on the synthetic TSC of the subject disclosure, that ratio is greater than 7.0 (e.g. 7.0 to 8.5, 7.0 to 8.7, or 7.0 to 9.0), advantageously greater than 7.5 (e.g. 7.5-8.5, 7.5 to 8.7, or 7.5 to 9.0), most advantageously greater than 8. The synthesized material is a "purer" or highly purified trans isomer.

Trans sodium crocetinate (TSC) was developed to cause reoxygenation of hypoxic tissues. TSC can be classified as a kosmotrope, compounds which increase the hydrogen bonding among water molecules. This, in turn, causes the water molecules to change from a random arrangement to one which more resembles the structure of crystals. More structure also results in a reduction in the density of water, allowing small molecules like oxygen or glucose to diffuse through the liquid phase more easily. Kosmotropes are also known to result in this structure formation at only certain, discrete concentrations.

Formulation and Administration

In formulating trans carotenoids including BTCSs such as trans sodium crocetinate (TSC) with other ingredients (excipients), it is advantageous to: improve the solubility (increase the concentration of the active agent (e.g. TSC) in solution), stability, bioavailability and isotonic balance of the BTC, increase the pH of an aqueous solution, and/or increase the osmolality of an aqueous solution. The excipient should act as an additive to prevent self aggregation of monomeric BTC units in solution, or to prevent pre-mature precipitation of BTC. The addition of the excipient should aid in at least one of these aspects. Bipolar trans carotenoid (BTC) molecules can be formulated in a variety of ways. A basic formulation is a mixture of the BTC in sterile water, administered by intravenous injection. This formulation can be modified through the inclusion of various pharmaceutical excipients, including the cyclodextrins. These formulations can also be administered by intravenous injection.

Any of the above described various liquid formulations can be freeze-dried (lyophilized) to form a dry powder with enhanced solubility and stability characteristics. Such powdered forms are then reconstituted for administration. One method is to reconstitute the powder in a liquid such as saline or sterile water for injection and then administer it by intravenous injection. This method can include the use of a multi-compartment syringe containing the powder in one compartment and liquid in the other compartment. Similarly, the product can be bottled in a vial containing a barrier separating the powder from the liquid. Before administration, the barrier is broken and the components mixed before intravenous injection.

In addition to intravenous injection, routes of administration for specially formulated trans carotenoid molecules include intramuscular injection, delivery by inhalation, oral administration and transdermal administration.

Cyclodextrins

In order to administer some pharmaceuticals, it is necessary to add another compound which will aid in increasing the absorption/solubility/concentration of the active pharmaceutical ingredient (API). Such compounds are called excipients, and cyclodextrins are examples of excipients. Cyclodextrins are cyclic carbohydrate chains derived from starch. They differ from one another by the number of glucopyranose units in their structure. The parent cyclodextrins contain six, seven and eight glucopyranose units, and are referred to as alpha, beta and gamma cyclodextrins respectively. Cyclodextrins were first discovered in 1891, and have been used as part of pharmaceutical preparations for several years.

Cyclodextrins are cyclic (alpha-1,4)-linked oligosaccharides of alpha-D-gluco-pyranose containing a relatively hydrophobic central cavity and hydrophilic outer surface. In the pharmaceutical industry, cyclodextrins have mainly been used as complexing agents to increase the aqueous solubility of poorly water-soluble drugs, and to increase their bioavailability and stability. In addition, cyclodextrins are used to reduce or prevent gastrointestinal or ocular irritation, reduce or eliminate unpleasant smells or tastes, prevent drug-drug or drug-additive interactions, or even to convert oils and liquid drugs into microcrystalline or amorphous powders.

Although the BTC compounds are soluble in water, the use of the cyclodextrins can increase that solubility even more so that a smaller volume of drug solution can be administered for a given dosage.

There are a number of cyclodextrins that can be used with the Compounds of the disclosure. See for example, U.S. Pat. No. 4,727,064, hereby incorporated by reference in its entirety. Advantageous cyclodextrins are gamma-cyclodextrin, 2-hydroxylpropyl-beta-cyclodextrin and 2-hydroxylpropyl-beta-cyclodextrin, or other cyclodextrins which enhance the solubility of the BTC.

The use of gamma-cyclodextrin with TSC increases the solubility of TSC in water by 3-7 times. Although this is not as large a factor as seen in some other cases for increasing the solubility of an active agent with a cyclodextrin, it is important in allowing for the parenteral administration of TSC in smaller volume dosages to humans (or animals). The incorporation of the gamma cyclodextrin also allows for TSC to be absorbed into the blood stream when injected intramuscularly. Absorption is quick, and efficacious blood levels of TSC are reached quickly (as shown in rats).

The cyclodextrin formulation can be used with other trans carotenoids and carotenoid salts. The subject disclosure also includes novel compositions of carotenoids which are not salts (e.g. acid forms such as crocetin, crocin or the intermediate compounds noted above) and a cyclodextrin. In other words, trans carotenoids which are not salts can be formulated with a cyclodextrin. Mannitol can be added for osmolality, or the cyclodextrin BTC mixture can be added to isotonic saline (see below).

The amount of the cyclodextran used is that amount which will contain the trans carotenoid but not so much that it will not release the trans carotenoid.

Cyclodextrin-Mannitol

A trans carotenoid such as TSC can be formulated with a cyclodextrin as noted above and a non-metabolized sugar such as mannitol (e.g. d-mannitol to adjust the osmotic pressure to be the same as that of blood). Solutions containing about 20 mg TSC/ml of solution can be made this way. This solution can be added to isotonic saline or to other solutions in order to dilute it and still maintain the proper osmolality. See Example 12 of U.S. Pat. No. 8,030,350 hereby incorporated by reference in its entirety.

Mannitol/Acetic Acid

A BTCS such as TSC can be formulated with mannitol such as d-mannitol, and a mild acid such as acetic acid or citric acid to adjust the pH. The pH of the solution should be around 8 to 8.5. It should be close to being an isotonic solution, and, as such, can be injected directly into the blood stream.

Water+Saline

A BTCS such as TSC can be dissolved in water (advantageously injectable sterile water). This solution can then be diluted with water, normal saline, Ringer's lactate or phosphate buffer, and the resulting mixture either infused or injected.

Buffers

A buffer such as glycine or bicarbonate can be added to the formulation at a level of about 50 mM (in the case of glycine) for stability of the BCT such as TSC.

TSC and Gamma-Cyclodextrin

The ratio of TSC to cyclodextrin is based on TSC:cyclodextrin solubility data. For example, 20 mg/ml TSC, 8% gamma cyclodextrin, 50 mM glycine, 2.33% mannitol with pH 8.2+/−0.5, or 10 mg/ml TSC and 4% cyclodextrin, or 5 mg/ml and 2% cyclodextrin. The ratios of these ingredients can be altered somewhat, as is obvious to one skilled in this art.

Mannitol can be used to adjust osmolality and its concentration varies depending on the concentration of other ingredients. The glycine is held constant. TSC is more stable at higher pHs. pH of around 8.2+/−0.5 is required for stability and is physiologically compatible. The use of glycine is compatible with lyophilization. Alternatively, the TSC and cyclodextrin is formulated using a 50 mM bicarbonate or other buffers, in place of the glycine.

Endotoxin Removal of Gamma-Cyclodextrin

Commercially available pharmaceutical grade cyclodextrin has endotoxin levels that are incompatible with intravenous injection. The endotoxin levels must be reduced in order to use the cyclodextrin in a BTC formulation intended for intravenous injection.

Lyophilization

Lyophilization can be used to produce an easily reconstituted injectable solution.

Chemotherapy Agents

It is contemplated that various chemotherapy agents can be used in the presently disclosed treatments and/or combination therapies. Chemotherapy agents are divided into classes. These are sometimes listed as Alkylating Agents including Platinum based compounds, Antimetabolites, Antitumor Antibiotics including Anthracyclines, Topoisomerase Inhibitors, and Anti-microtubule Agents (Mitotic Inhibitors). Other classifications also exist. It is contemplated that any of the following classes may be used together with the present compositions and methods of treatment.

Alkylating Agents

Alkylating agents are the oldest group of chemotherapeutics in use today. Originally derived from mustard gas used in World War I, there are now many types of alkylating agents in use.[1] They are so named because of their ability to alkylate many molecules, including proteins, RNA and DNA. This ability to bind covalently to DNA via their alkyl group is the primary cause for their anti-cancer effects. DNA is made of two strands and the molecules may either bind twice to one strand of DNA (intra-strand crosslink) or may bind once to both strands (interstrand crosslink). If the cell tries to replicate crosslinked DNA during cell division, or tries to repair it, the DNA strands can break. This leads to a form of programmed cell death called apoptosis. Alkylating agents will work at any point in the cell cycle and thus are known as cell cycle-independent drugs. For this reason, the effect on the cell is dose dependent; the fraction of cells that die is directly proportional to the dose of drug.

The subtypes of alkylating agents are the nitrogen mustards, nitrosoureas, tetrazines, aziridines, cisplatins and derivatives, and non-classical alkylating agents. Nitrogen mustards include mechlorethamine, cyclophosphamide, melphalan, chlorambucil, ifosfamide and busulfan. Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide. Aziridines include thiotepa, mytomycin and diaziquone (AZQ). Cisplatin and derivatives include cisplatin, carboplatin and oxaliplatin. They impair cell function by forming covalent bonds with the amino, carboxyl, sulfhydryl, and phosphate groups in biologically important molecules. Non-classical alkylating agents include procarbazine and hexamethylmelamine.

Examples of alkylating agents include: altretamine, busulfan, carboplatin, carmustine, chlorambucil, cisplatin, cyclophosphamide, dacarbazine, lomustine, melphalan, oxalaplatin, temozolomide, and thiotepa.

Antimetabolites

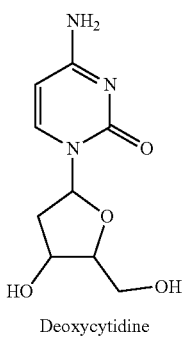

Deoxycytidine

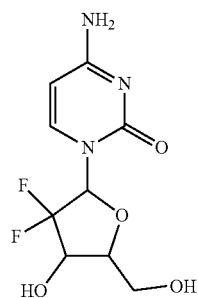

Gemcitabine

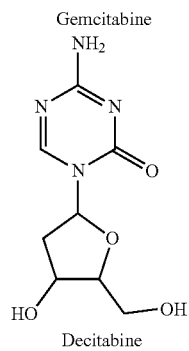

Decitabine

Deoxycytidine (left) and two anti-metabolite drugs (center and right); Gemcitabine and Decitabine. The drugs are very similar but they have subtle differences in their chemical groups.

Anti-metabolites are a group of molecules that impede DNA and RNA synthesis. Many of them have a similar structure to the building blocks of DNA and RNA. The building blocks are nucleotides; a molecule comprising a nucleobase, a sugar and a phosphate group. The nucleobases are divided into purines (guanine and adenine) and pyrimidines (cytosine, thymine and uracil). Anti-metabolites resemble either nucleobases or nucleosides (a nucleotide without the phosphate group), but have altered chemical groups. These drugs exert their effect by either blocking the enzymes required for DNA synthesis or becoming incorporated into DNA or RNA. By inhibiting the enzymes involved in DNA synthesis, they prevent mitosis because the DNA cannot duplicate itself. Also, after misincorporation of the molecules into DNA, DNA damage can occur and programmed cell death (apoptosis) is induced. Unlike alkylating agents, anti-metabolites are cell cycle dependent. This means that they only work during a specific part of the cell cycle, in this case S-phase (the DNA synthesis phase). For this reason, at a certain dose, the effect plateaus and proportionally no more cell death occurs with increased doses. Subtypes of the anti-metabolites are the anti-folates, fluoropyrimidines, deoxynucleoside analogues and thiopurines.

The anti-folates include methotrexate and pemetrexed. Methotrexate inhibits dihydrofolate reductase (DHFR), an enzyme that regenerates tetrahydrofolate from dihydrofolate. When the enzyme is inhibited by methotrexate, the cellular levels of folate coenzymes diminish. These are required for thymidylate and purine production, which are both essential for DNA synthesis and cell division. Pemetrexed is another anti-metabolite that affects purine and pyrimidine production, and therefore also inhibits DNA synthesis. It primarily inhibits the enzyme thymidylate synthase, but also has effects on DHFR, aminoimidazole carboxamide ribonucleotide formyltransferase and glycinamide ribonucleotide formyltransferase. The fluoropyrimidines include fluorouracil and capecitabine. Fluorouracil is a nucleobase analogue that is metabolised in cells to form at least two active products; 5-fluourouridine monophosphate (FUMP) and 5-fluoro-2'-deoxyuridine 5'-phosphate (fdUMP). FUMP becomes incorporated into RNA and fdUMP inhibits the enzyme thymidylate synthase; both of which lead to cell death. Capecitabine is a prodrug of 5-fluorouracil that is broken down in cells to produce the active drug. The deoxynucleoside analogues include cytarabine, gemcitabine, decitabine, Vidaza, fludarabine, nelarabine, cladribine, clofarabine and pentostatin. The thiopurines include thioguanine and mercaptopurine.

Examples of antimetabolites include: 5-fluorouracil (5-FU), 6-mercaptopurine (6-MP), capecitabine (Xeloda®), cytarabine (Ara-C®), floxuridine, fludarabine, gemcitabine (Gemzar®), hydroxyurea, methotrexate, and pemetrexed (Alimta®).

Anti-Microtubule Agents

Vinca alkaloids prevent the assembly of microtubules, whereas taxanes prevent their disassembly. Both mechanisms cause defective mitosis.

Anti-microtubule agents are plant-derived chemicals that block cell division by preventing microtubule function. Microtubules are an important cellular structure composed of two proteins; α-tubulin and β-tubulin. They are hollow rod shaped structures that are required for cell division, among other cellular functions. Microtubules are dynamic structures, which means that they are permanently in a state of assembly and disassembly. Vinca alkaloids and taxanes are the two main groups of anti-microtubule agents, and although both of these groups of drugs cause microtubule dysfunction, their mechanisms of action are completely opposite. The vinca alkaloids prevent the formation of the microtubules, whereas the taxanes prevent the microtubule disassembly. By doing so, they prevent the cancer cells from completing mitosis. Following this, cell cycle arrest occurs, which induces programmed cell death (apoptosis). Also, these drugs can affect blood vessel growth; an essential process that tumours utilise in order to grow specific. They bind to the tubulin molecules in S-phase and prevent proper microtubule formation required for M-phase.

Taxanes are natural and semi-synthetic drugs. The first drug of their class, paclitaxel, was originally extracted from the Pacific Yew tree, *Taxus brevifolia*. This drug and another in this class, docetaxel, are produced semi-synthetically from a chemical found in the bark of another Yew tree; *Taxus baccata*. These drugs promote microtubule stability, preventing their disassembly. Paclitaxel prevents the cell cycle at the boundary of G2-M, whereas docetaxel exerts its effect during S-phase. Taxanes present difficulties in formulation as medicines because they are poorly soluble in water.

Podophyllotoxin is an antineoplastic lignan obtained primarily from the American Mayapple (*Podophyllum peltatum*) and Himalayan Mayapple (*Podophyllum hexandrum* or *Podophyllum emodi*). It has anti-microtubule activity, and its mechanism is similar to that of vinca alkaloids in that they bind to tubulin, inhibiting microtubule formation. Podophyllotoxin is used to produce two other drugs with different mechanisms of action: etoposide and teniposide.

Examples of mitotic inhibitors include: docetaxel, estramustine, ixabepilone, paclitaxel, vinblastine, vincristine, and vinorelbine.

Topoisomerase Inhibitors

Topoisomerase inhibitors are drugs that affect the activity of two enzymes: topoisomerase I and topoisomerase II. When the DNA double-strand helix is unwound, during DNA replication or transcription, for example, the adjacent unopened DNA winds tighter (supercoils), like opening the middle of a twisted rope. The stress caused by this effect is in part aided by the topoisomerase enzymes. They produce single- or double-strand breaks into DNA, reducing the tension in the DNA strand. This allows the normal unwinding of DNA to occur during replication or transcription. Inhibition of topoisomerase I or II interferes with both of these processes.

Two topoisomerase I inhibitors, irinotecan and topotecan, are semi-synthetically derived from camptothecin, which is obtained from the Chinese ornamental tree *Camptotheca acuminata*. Drugs that target topoisomerase II can be divided into two groups. The topoisomerase II poisons cause increased levels enzymes bound to DNA. This prevents DNA replication and transcription, causes DNA strand breaks, and leads to programmed cell death (apoptosis). These agents include etoposide, doxorubicin, mitoxantrone and teniposide. The second group, catalytic inhibitors, are drugs that block the activity of topoisomerase II, and therefore prevent DNA synthesis and translation because the DNA cannot unwind properly. This group includes novobiocin, merbarone, and aclarubicin, which also have other significant mechanisms of action.

Topoisomerase inhibitors are grouped according to which type of enzyme they affect:

Topoisomerase I inhibitors include: topotecan, and irinotecan (CPT-11).

Topoisomerase II inhibitors include: etoposide (VP-16), teniposide, and mitoxantrone (also acts as an anti-tumor antibiotic).

Cytotoxic Antibiotics

The cytotoxic antibiotics are a varied group of drugs that have various mechanisms of action. The group includes the anthracyclines and other drugs including actinomycin, bleomycin, plicamycin, and mitomycin. Doxorubicin and daunorubicin were the first two anthracyclines, and were obtained from the bacterium *Streptomyces peucetius*. Derivatives of these compounds include epirubicin and idarubicin. Other clinically used drugs in the anthracyline group are pirarubicin, aclarubicin, and mitoxantrone. The mechanisms of anthracyclines include DNA intercalation (molecules insert between the two strands of DNA), generation of highly reactive free radicals that damage intercellular molecules and topoisomerase inhibition. Actinomycin is a complex molecule that intercalates DNA and prevents RNA synthesis. Bleomycin, a glycopeptide isolated from *Streptomyces verticillus*, also intercalates DNA, but produces free radicals that damage DNA. This occurs when bleomycin binds to a metal ion, becomes chemically reduced and reacts with oxygen. Mitomycin is a cytotoxic antibiotic with the ability to alkylate DNA.

Anthracyclines: Anthracyclines are anti-tumor antibiotics that interfere with enzymes involved in copying DNA during the cell cycle. (Enzymes are proteins that start, help, or speed up the rate of chemical reactions in cells.) They are widely used for a variety of cancers.

Examples of anthracyclines include: daunorubicin, doxorubicin (Adriamycin®), epirubicin, and idarubicin.

A major concern when giving these drugs is that they can permanently damage the heart if given in high doses. For this reason, lifetime dose limits are often placed on these drugs.

Anti-tumor antibiotics that are not anthracyclines include: actinomycin-D, bleomycin, mitomycin-C, and mitoxantrone (also acts as a topoisomerase II inhibitor, see below).

Other Drugs

In another embodiment, one or more benzo[c]chromen-6-one derivative such as SG-529, is administered prior to, during, or after radiation therapy and/or chemotherapy. See U.S. Pat. No. 8,475,776 hereby incorporated by reference in its entirety.

Radiation Therapy

It is contemplated that radiation therapy may be used together with a bipolar trans carotenoid salt (e.g., TSC) in the treatment of a tumor or cancer. The following is a brief description of types of radiation therapy that may be used with the disclosed compositions and in the disclosed methods of treatment.

External-Beam Radiation Therapy

This is the most common type of radiation treatment. It delivers radiation from a machine located outside the body. It can treat large areas of the body, if needed. The machine used to create the radiation beam is called a linear accelerator or linac. Computers with special software adjust the size and shape of the beam. They also direct the beam to target the tumor while avoiding the healthy tissue near the cancer cells. External-beam radiation therapy does not make you radioactive.

Types of external-beam radiation therapy include:

- Three-dimensional conformal radiation therapy (3D-CRT): As part of this treatment, special computers create detailed three-dimensional pictures of the cancer. This allows the treatment team to aim the radiation more precisely. By doing this, they can use higher doses of radiation while reducing the risk of damaging healthy tissue. Studies have shown that 3D-CRT can lower the risk of side effects. For instance, it can limit the damage to the salivary glands, which can cause dry mouth when people with head and neck cancer have radiation therapy.
- Intensity modulated radiation therapy (IMRT): This treatment directs the radiation dose at the tumor better than 3D-CRT by varying the intensity of the beam. IMRT protects healthy tissues from radiation better than 3D-CRT.
- Proton beam therapy: This treatment uses protons, rather than x-rays, to treat some cancers. Protons are parts of atoms that at high energy can destroy cancer cells. Directing protons at a tumor decreases the amount of radiation sent to nearby healthy tissue, reducing damage to this tissue. Because this therapy is relatively new and requires special equipment, it is not available at every medical center. The potential benefits of proton therapy compared to IMRT have not been established for some cancers, such as prostate cancer.
- Stereotactic radiation therapy: This treatment delivers a large, precise radiation dose to a small tumor area. Because of the precision involved in this type of treatment, the patient must remain very still. Head frames or individual body molds are used to limit movement. Although this therapy is often given as a single treatment, some patients may need several radiation treatments.

Internal Radiation Therapy

This type of radiation treatment is also known as brachytherapy. Radioactive material is placed into the cancer itself or into the tissue surrounding it. These implants may be permanent or temporary and may require a hospital stay. Permanent implants are tiny steel seeds about the size of a grain of rice that contain radioactive material. These capsules are placed inside the body at the tumor site. The seeds deliver most of the radiation around the area of the implant. However, some radiation can be released from the patient's body. This means the patient should take precautions to protect others from radiation exposure while the seeds are active. Over time, the implant loses its radioactivity, but the inactive seeds remain in the body.

Methods of Treatment

Cancer

The subject disclosure relates to the treatment of various tumors and/or cancers (i.e., gliobastoma, pancreatic cancer, etc.). It is well established that tumors are hypoxic with many tumor types being highly hypoxic. Further, it is known that hypoxic tumors are more resistant to radiotherapy and chemotherapy. Through HIF1 alpha up-regulation, hypoxia is associated with multiple negative effects that lead to aggressive tumor phenotypes. These effects include increased angiogenesis, increased metastasis, as well as increased resistance to chemotherapy and radiation therapy. Hypoxia via HIF1a affects many genes involved in cancer progression. Bipolar trans carotenoids such as TSC alter expression of HIF1 targeted genes in hypoxic conditions. For example, studies have shown that the VEGF A gene which is upregulated with hypoxia is down regulated with TSC.

The methods of the subject disclosure are directed to administering a dose of a bipolar trans carotenoid such as TSC, at a dose and at the proper time prior to administration of chemotherapy or radiation therapy (as discussed above) such that the oxygen partial pressure is elevated inside the tumor while the chemotherapy or radiation therapy is administered so as to obtain maximum increased killing effect of the chemotherapy and or radiotherapy on the cancer cells/tumor. The administration of the bipolar trans carotenoid, due to its hypoxia reducing ability, can also decrease angiogenesis, decrease metastasis, and down regulate HIF1a production in the tumor.

Chemotherapy (chemo) uses anti-cancer drugs injected into a vein or taken by mouth. These drugs enter the bloodstream and reach all areas of the body, making this treatment useful for cancers that have spread beyond the organ in which they started.

- Chemotherapy can be given before surgery (sometimes along with radiation) to shrink the tumor. This is known as neoadjuvant treatment.
- Chemotherapy can be used after surgery (sometimes along with radiation) to try to kill any cancer cells that have been left behind (but can't be seen). This type of treatment, called adjuvant treatment, lowers the chance that the cancer will come back later.
- Chemotherapy is commonly used when the cancer is advanced and can't be removed completely with surgery.

When chemotherapy is given along with radiation, it is known as chemoradiation or chemoradiotherapy. It can improve the effectiveness of the radiation, but it also may cause more severe side effects.

Doctors give chemotherapy in cycles, with each period of treatment followed by a rest period to allow the body time to recover. Each chemotherapy cycle typically lasts for a few weeks.

With bipolar trans carotenoids such as TSC, there are discrete concentrations that produce efficacy in causing maximum oxygen partial pressure in animals or humans. It has been found for all animals tested (including humans), that two such efficacious dosages exist: a "low dose" and a "high dose." For humans, a low dose of 0.15-0.35 mg/kg, e.g. 0.25 mg/kg, produces the maximum reoxygenation of hypoxic tissue 50 minutes after injection, a change that lasts for a short time, while a high dose of 0.75-2.0 mg/kg, e.g. 1.5 mg/kg, produces the same maximum change but which lasts for over an hour. Increasing the oxygen levels in the cancerous tissue while administering chemotherapy or radiotherapy results in superior cancerous tissue (tumor) killing.

In addition to enhancing the cytotoxicity of chemotherapeutic agents in a tumor, administration of a bipolar trans carotenoid such as TSC can reduce or treat the neurotoxicity or neuropathy that the chemotherapy agents can cause.

Pancreatic Cancer

The various types of pancreatic cancer are discussed earlier in this specification. Chemotherapy can be used at any stage of these pancreatic cancers.

Pancreatic tumors are usually highly hypoxic. Hypoxia results in impairment of the tumor response to chemotherapy agents including antimetabolites such as gemcitabine.

Many different chemo drugs can be used to treat pancreatic cancer, including: gemcitabine (Gemzar®), 5-fluorouracil (5-FU), irinotecan (Camptosar®), oxaliplatin (Eloxatin®), albumin-bound paclitaxel (nab-paclitaxel) (Abraxane®), capecitabine (Xeloda®), cisplatin, paclitaxel (Taxol®), docetaxel (Taxotere®), and irinotecan liposome (Onivyde®).

In people who are healthy enough, 2 or more drugs are usually given together. The current standard of care for patients with metastatic pancreatic cancer includes gemcitabine combined with either erlotinib or nab-paclitaxel. Erlotinib is approved for the treatment of metastatic non-small cell lung cancer and metastatic pancreatic cancer. Nab-paclitaxel is approved for the treatment of breast cancer, non-small cell lung cancer, and metastatic pancreatic cancer.

Other examples of combo therapies are gemcitabine and capecitabine (Xeloda), or gemcitabine, irinotecan, and celecoxib (an arthritis drug). Another combo regimen is the Folfirinox (leucovorin+5-fluorouracil+oxaliplatin+irinotecan) regimen.

For people who are not healthy enough for combined treatments, a single drug (usually gemcitabine, 5-FU, or capecitabine) can be used.

Advantageous treatment of such tumors includes administration of a high dose—0.75-2.0 mg/kg—of a bipolar trans carotenoid such as TSC, 1-2 hr. prior to administration of one or more chemotherapy agents. A typical cycle would be administration of TSC and the chemotherapy agent (e.g. gemcitabine), or agents (gemcitabine followed directly by nab-paclitaxel), once per week for 3 weeks followed by a week of rest. This cycle can be repeated the following month or months.

In an advantageous embodiment where two chemotherapy agents (nab-paclitaxel and gemcitabine) are given sequentially, TSC (1.5 mg/kg) is given IV as a bolus 45-60 minutes before beginning infusion of 125 mg/m2 nab-paclitaxel (30-40 min). The IV infusion of 1000 mg/m2 gemcitabine (30-40 min.) starts soon after the IV infusion of nab-paclitaxel. For example, once per week for three weeks, TSC is administered IV bolus 60 minutes before start of the IV infusion of the nab-paclitaxel, and 90 minutes prior to the start of the IV infusion of the gemcitabine (allotting 30 minutes for administration of each of the chemotherapeutic agents). The effect of the TSC (increasing the oxygen partial pressure in the tumor) will then last for the duration of both chemotherapy drugs. The 3 weeks of the administration above is followed by a week of rest.

Radiation therapy utilizing the 0.15-0.35 mg/kg dose of TSC prior to administration of the RT can also be used in the treatment of pancreatic cancer.

Gliobastoma Multiforme

Glioblastoma tumors are highly hypoxic. TSC can be used to enhance the effects of both the radiation therapy (RT) and chemotherapy (e.g. alkylating agent or antimetabolite such as temozolomide (TMZ)). Advantageous treatment of GBM tumors includes administration of a bipolar trans carotenoid such as TSC at a dose of 0.15-0.35 mg/kg, prior to, advantageously 45-60 min. prior to, administration of radiotherapy (optionally a chemotherapy agent such as temozolomide is administered, usually the night preceding RT). The TMZ is typically administered daily for the duration of the RT sessions. The bipolar trans carotenoid, e.g. TSC, dosage during radiation therapy is advantageously 0.25 mg/kg given 45 minutes before radiation.

The bipolar trans carotenoid, e.g. TSC dosage during chemotherapy (without radiation) is advantageously 1.5 mg/kg given 1-2 hrs. before the chemotherapeutic agent. For temozolomide administration (5 daily administrations during the monthly week of chemotherapy), the bipolar trans carotenoid is typically administered 2-5 times (advantageously 3 times) during the monthly week. The monthly bipolar trans carotenoid and chemo cycle can continue for 6 or more months.

In an advantageous embodiment, after surgery to remove that portion of the GBM tumor feasibly removed, a bipolar trans carotenoid such as TSC is infused at a dose of 0.25 mg/kg. 45-60 minutes prior to radiation therapy—(2 Gy) 5 days a week for 6 weeks. Temozolomide is administered (e.g. 75 mg/m2 temozolomide) per day 7 days per week for the duration of RT. The TSC treatment occurs 3 times per week for the six weeks. After a rest period of 1-4 weeks, for another 6 month period, the TSC is injected at a dose of 1.5 mg/kg 1-2 hr. prior to chemotherapy (e.g. temozolomide 150-200 mg/m2 on 5 consecutive days for the first week of the month). This TSC administration occurs 3 times per week for the first week of the month for the following 6 months. For a 6-week radiation therapy regimen followed by a 6-month chemotherapy regimen, this results in 36 doses of TSC—18 during radiation/chemotherapy (6 weeks), and 18 during chemotherapy (6 months).

Brain Metastases

Treatment for brain metastases involves both controlling the symptoms associated with the condition as well as attacking the cancer directly. Brain metastases typically result in edema that can be controlled with the use of steroids; however, long-term use of steroids typically results in side effects that greatly diminishes a patient's quality of life. Approximately 25-45% of patients will experience seizures and require the use anti-epileptic drugs. Surgery is only utilized in patients with a solitary brain metastatic lesion. Radiation therapy remains the standard of care for the vast majority of patients with brain metastases.

Brain metastases are typically hypoxic. Radiation therapy remains the standard of care for the vast majority of patients with brain metastases. Advantageous treatment of such tumors includes administration of a bipolar trans carotenoid such as TSC at a dose of 0.15-0.35 mg/kg, e.g. 0.25 mg/kg, 45-60 minutes prior to administration of radiotherapy. In another embodiment, the methods described above for GBM, i.e. use of a chemo agent as well as radiation therapy, are also applicable to treatment of brain metastases.

Other Cancers

Other cancers that can be treated according to the methods of the subject disclosure include solid tumors such as squamous cell carcinomas, melanomas, lymphomas, sarcomas, sarcoids, osteosarcomas, skin cancer, breast cancer, head and neck cancer, gynecological cancer, urological and male genital cancer, bladder cancer, prostate cancer, bone cancer, cancers of the endocrine glands (e.g., pancreatic cancer), cancers of the alimentary canal, cancers of the major digestive glands/organs, CNS cancer, and lung cancer.

Advantageous modes of treating the above cancers include the standard of care for a given cancer indication supplemented by administration of a bipolar trans carotenoid such as TSC at a dose of 0.75-2.0 mg/kg, e.g. 1.5 mg/kg, prior to administration of chemotherapy, and 0.15-0.35 mg/kg, e.g. 0.25 mg/kg, of TSC prior to administration of radiotherapy.

Non-Cancer Uses

It has also been determined that several non-cancer disorders are beneficially treated utilizing an administration regimen of a bipolar trans carotenoid such as TSC, as described below. Pre-clinical efficacy studies using TSC have demonstrated the following:

| Species | Condition | Best Dosage |
| --- | --- | --- |
| Rat | Hemorrhagic Shock | Low |
| Rat | Ischemic Stroke | Low |
| Rat | Hemorrhagic Stroke | Low |
| Rat | Cancer: Radiation Sensitizer | Low |
| Rat | Cancer Chemosensitizer | High |
| Rat | Parkinson's Disease | High |
| Rat | Memory Recall | High |
| Mouse | Cancer: Radiation Sensitizer | Low |
| Mouse | Critical Limb Ischemia | High |
| Rabbit | Ischemic Stroke | Low |
| Pig | Hemorrhagic Shock | Low |
| Pig | Myocardial Infarction | Low |
| Pig | Wound Healing | High |

For humans, TSC at the low dosage e.g. 0.15-0.35 mg/kg, e.g. 0.25 mg/kg, is administered IV for treating cardiovascular events including stroke, myocardial infarction or hemorrhagic shock (blood loss). See U.S. Pat. No. 7,919,527 hereby incorporated by reference in its entirety.

TSC at the high dose 0.75-2.0 mg/kg, e.g.1.5 mg/kg, can act as a neuroprotective agent for humans for treating CNS conditions (Alzheimer's, Parkinson's, memory loss), as well as for promoting wound healing and alleviating extreme limb ischemia. See U.S. Pat. Nos. 7,759,506 and 8,293,804 each of which is hereby incorporated in its entirety. Advantageous administration is orally, 2-5 times per week at a dose that achieves TSC levels equivalent to 0.75-2 mg/kg given IV. See commonly owned U.S. Pat. No. 8,974,822 hereby incorporated by reference in its entirety.

The following Examples are illustrative, but not limiting of the compounds, compositions and methods of the present disclosure. Other suitable modifications and adaptations of a variety of conditions and parameters normally encountered which are obvious to those skilled in the art are within the spirit and scope of this disclosure.

EXAMPLES

DMBA Tumors

Breast tumors were induced through injection of DMBA (dimethylbenzantracene) under the mammary tissue of female rats. The tumors usually grow in most rats and reach measurable conditions after 10 days.

The following studies used a method in which a 3-mL syringe is filled first with 1 ml of DMBA dissolved in sunflower seed oil (20 mg DMBA per mL of solution). Following that, 2 mL's of air are pulled into the syringe. The needle of the syringe is then inserted under the mammary tissue near a hind leg and the air in the syringe is carefully injected. The injection of the air forms a "pocket", and then the 1 mL of DMBA solution is injected into that pocket.

After the tumors have grown up (about 10 days), their volumes are estimated by measuring the diameter (d) and the length (L) of the football-shaped tumors formed. This is done using calipers after feeling the tumor with one's fingers. To estimate the volume of the tumor, you multiply the diameter squared times the length and divide by 2:

$$\text{Tumor volume (in mm3)} = \{(d \text{ in mm})^2 2\} \times (L \text{ in mm})$$

TSC or saline (controls) was injected in the tail vein of the rats at a volume of 0.1 mL and a dose of 0.25 mg/kg TSC about 1-2 hours before the chemotherapeutic agent was injected intraperitoneally (IP) in the rats.

Example 1: Platinum-Containing Compounds (Cisplatin)

In order to understand which dosages are efficacious when used with chemotherapy, a rat model of breast tumors was used. The model involves injecting the chemical dimethylbenzanthracene (DMBA) under the mammary gland of a female Sprague-Dawley rat. After a few days, tumors begin to grow and can be measured by feeling the football-shaped tumor under the skin and measured using calipers.

In this study, a platinum based compound was used (cisplatin). The low dose (for rats) 0.1 mg/kg of TSC given (IV) 50 minutes before chemotherapy was not effective in the study, but the high dose (for rats) 0.25 mg/kg of TSC given 2 hours before chemotherapy was efficacious as shown in the figure below.

Figure 2:
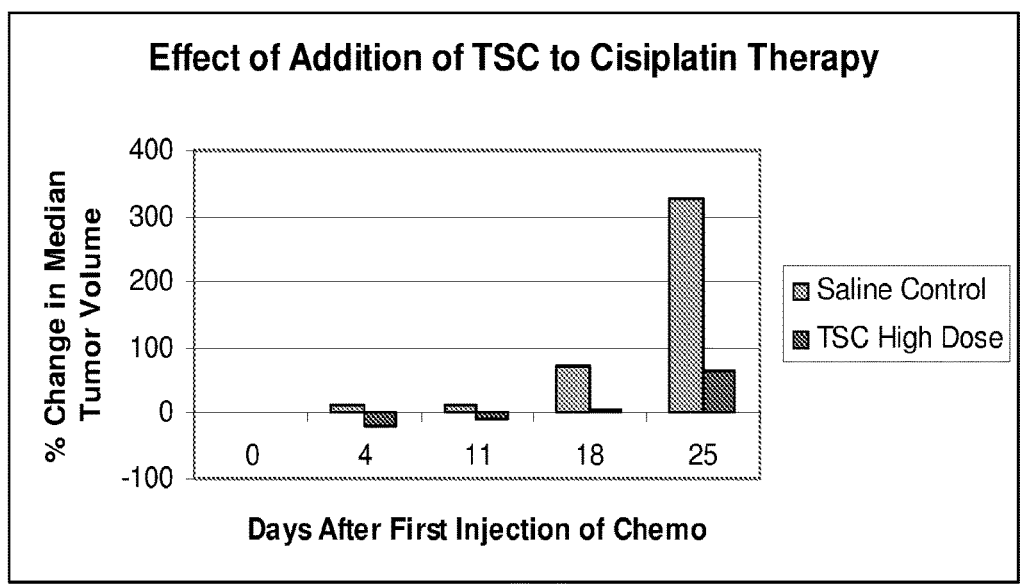
FIG. 2 illustrates the observed effect that a combination therapy of TSC and cisplatin had on tumor volume, which is discussed in Example 1.

High Dose of TSC given 2 hours before 1 mg/kg cisplatin. Cisplatin (1 mg/kg) was injected IP on days 0, 4, 11, 18. As shown in FIG. 2, rats treated with high dose TSC and cisplatin showed significant improvement in tumor volume over the control.

Example 2 Antimetabolites (Gemcitabine)

Figure 3:
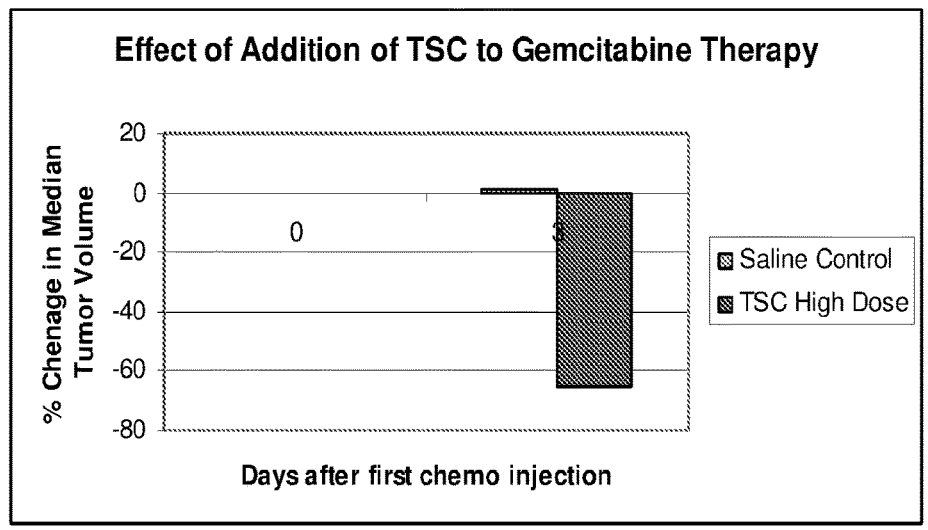
FIG. 3 illustrates the observed effect that a combination therapy of TSC and gemcitabine (10 mg/kg) had on tumor volume, which is discussed in Example 2.

In this study, the antimetabolite (gemcitabine) was used. The low dose of TSC given 50 minutes before chemotherapy was not effective in the study, but the high dose of TSC given 2 hours before chemotherapy was efficacious as shown in FIG. 3. The concentrations of the low dose TSC and the high dose TSC are the same as those defined in Example 1.

High Dose of TSC given 2 hours before 10 mg/kg gemcitabine. Gemcitabine (10 mg/kg) was injected IP on days 0, 3. As shown in FIG. 3, rats treated with high dose TSC and gemcitabine showed a significant decrease in tumor volume on day 3. For comparison, rats in the control group showed only a marginal increase in tumor volume. Most rats in both groups were dead on Day 6. Gemcitabine dose was cut in half, and the same behavior was seen.

Figure 4:
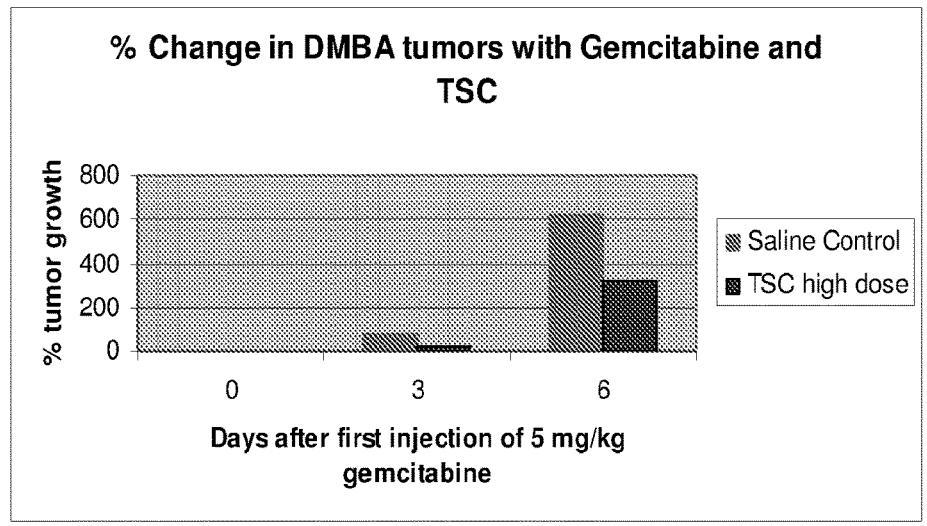
FIG. 4 illustrates the observed effect that a combination therapy of TSC and gemcitabine (5 mg/kg) had on tumor volume, which is discussed in Example 2.

High dose of TSC given 2 hours before 5 mg/kg gemcitabine. Gemcitabine (5 mg/kg) was injected IP on days 0, 3: Most rats in both groups were dead on Day 7. Results are shown in FIG. 4. Rats given high dose TSC and gemcitabine showed substantially less tumor growth than those in the control group. Note that % tumor growth for both groups is greater that for gemcitabine dosage of 10 mg/kg.

Time of TSC injection relative to that of the chemotherapy agent was tried with a gemcitabine dose of 7.5 mg/kg, but data obtained only for Day 2 after injection of gemcitabine because of its toxicity in rats. Dosing 2 hours before the chemotherapy is best although all methods reduced tumor growth relative to control.

Figure 5:
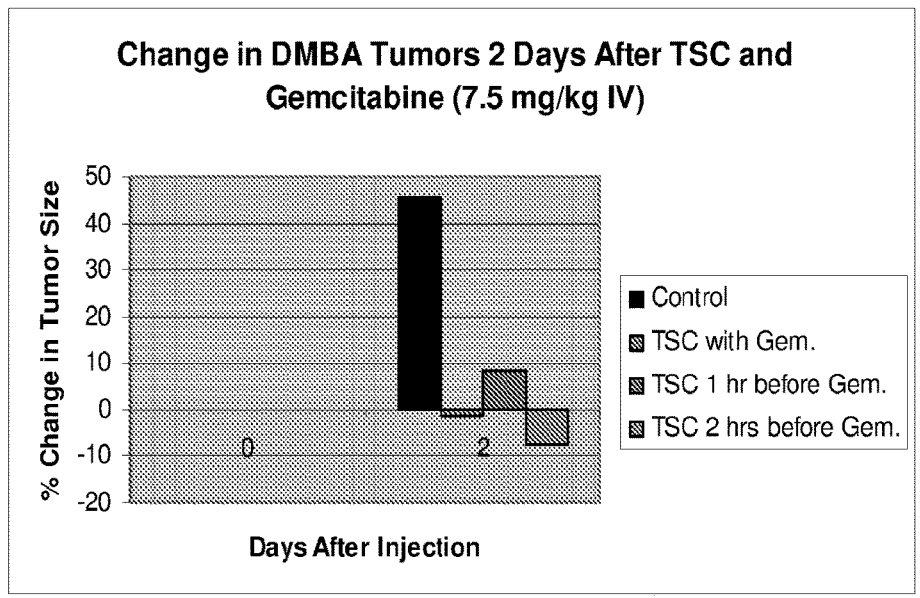
FIG. 5 illustrates the observed effect that a combination therapy of TSC and gemcitabine (7.5 mg/kg) had on tumor volume, which is discussed in Example 2.

High dose of TSC given 2 hours before 7.5 mg/kg gemcitabine. TSC high dose given i) concurrently, ii) 1 hour before, and iii) 2 hours before gemcitabine (7.5 mg/kg, given IV). As shown in FIG. 5, timing of TSC administration 2 hours prior to chemotherapeutic agent gives best results in all studies.

Example 3 Alkylating Agents (Temozolomide)

Figure 6:
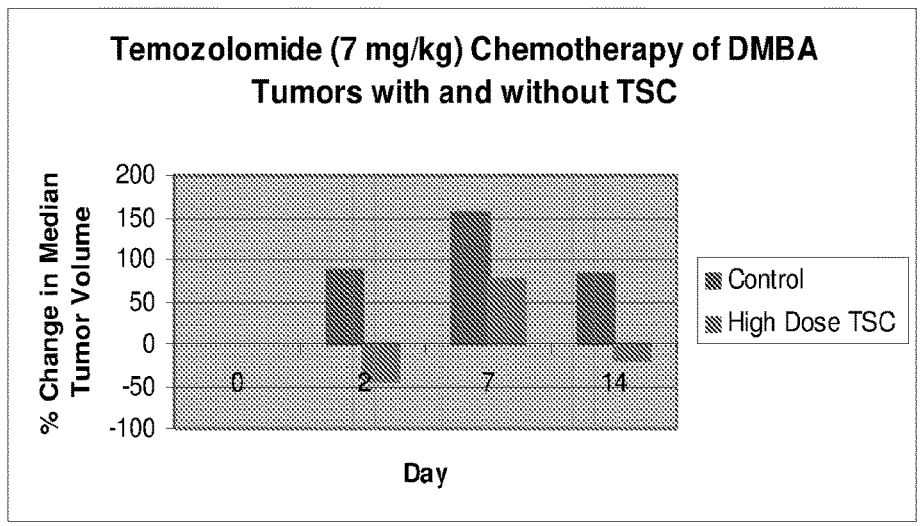
FIG. 6 illustrates the observed effect that a combination therapy of TSC and temozolomide had on tumor volume, which is discussed in Example 3.

A high dose of TSC as defined in Example 1 was given 2 hours prior to chemotherapy with temozolomide. Results are summarized in FIG. 6. Note that pseudoprogression was seen in this study, which accounts for the increase in tumor volume in subjects administered TSC together with temozolomide on day 7. Pseudoprogression is also seen in human chemotherapy of glioblastoma when using temozolomide as a radio- and chemo-sensitizer.

Example 4 Anti-Tumor Antibiotics—Anthracyclines (Doxorubicin)

Figure 7:
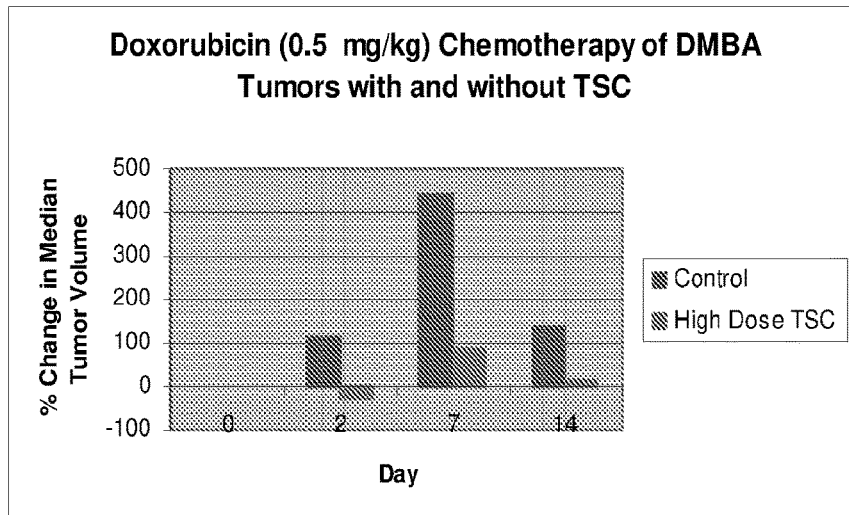
FIG. 7 illustrates the observed effect that a combination therapy of TSC and doxorubicin had on tumor volume, which is discussed in Example 4.

A high dose of TSC as defined in Example 1 was given 2 hours prior to chemotherapy with doxorubicin. Pseudoprogression was also seen in this study, which accounts for the increase in tumor volume in subjects administered TSC together with doxorubicin on day 7. The results, summarized in FIG. 7, show a marked reduction in tumor growth in comparison with the control group.

Example 5 Mitotic Inhibitors—Taxanes (Paclitaxel)

Figure 8:
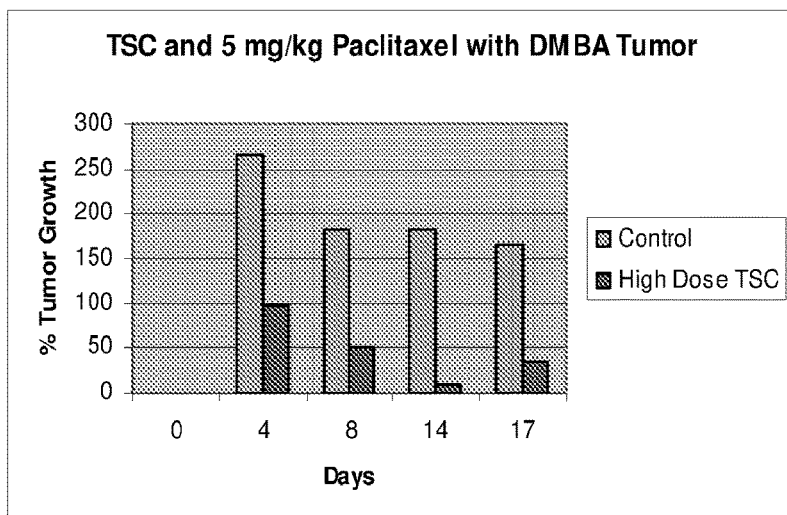
FIG. 8 illustrates the observed effect that a combination therapy of TSC and paclitaxel had on tumor volume, which is discussed in Example 5.

A high dose of TSC as defined in Example 1 was given 2 hrs. prior to chemotherapy with paclitaxel. Doses of chemotherapy and TSC were given on Days 0, 4, 8, 14. Pseudoprogression was also seen in this study. The results, summarized in FIG. 8, show a marked reduction in tumor growth in comparison with the control group.

Example 6 Trans Sodium Crocetinate Phase ½ Clinical Trial in GBM

To date, TSC has been used in 148 human subjects inhase 1 and Phase 2 clinical trials, with no serious adverse events reported. A Phase ½ clinical trial was recently completed examining TSC in patients with GBM. The Phase ½ clinical trial in GBM enrolled 59 patients with newly diagnosed disease that received TSC in conjunction with radiation therapy (RT) and temozolomide (TMZ). In the Phase I portion of the trial TSC was initially administered three times per week at half-dose to three patients prior to radiation. Six additional patients received full dose TSC for six weeks in combination with radiation. No dose-limiting toxicities were identified in the nine patients during the Phase I portion of the trial. Fifty additional patients were enrolled in the Phase II trial at full dose TSC in combination with TMZ and RT. Four weeks after completion of RT, all patients resumed TMZ for five days every four weeks, but no further TSC was administered.

More specifically, fifty-nine patients with newly-diagnosed GBM were enrolled. Patients received standard of care (SOC) radiation therapy (RT) (2 Gy/day, 5 days/week for 6 weeks) and TMZ (75 mg/m2) starting within 5 weeks after a surgical resection of their tumor, if such surgery were possible. Patients receiving only needle biopsies (i.e., no surgery) were also enrolled.

In addition to the SOC, TSC was administered 3 times per week, 0.25 mg/kg IV, usually on Monday, Wednesday and Friday, about 45 minutes prior to the RT sessions.

Four weeks after completion of RT, patients began chemotherapy with TMZ for 5 days of the first week of a 4 week cycle. This continued for 6 such cycles. No TSC was administered during this chemotherapy.

Overall Survival

Using the values reported for certain time points in the SOC analysis (Stupp R, et al.: Radiotherapy plus concomitant and adjuvant temozolomide for glioblastoma. N. Engl. J. Med. 352:987-996, 2005), as shown in Table 2 below, it was determined that survival was 10% greater in the TSC trial (i.e., the present study) at both 1 and 2 years than the rate in the historical trial, which had established the SOC for GBM in 2005.

TABLE 2

Overall Survival from Kaplan-Meier Analysis

| Time | Observed Survival Rate with TSC Treatment | Historical Survival Rate (from Stupp study) |
|---|---|---|
| 1 year | 71.2% | 61.1% |
| 2 years | 36.3% | 26.5% |

Both the 1- and 2-year survivals in the current trial fall outside the Stupp confidence intervals for those time points, suggesting statistical differences. That is, one can be 95% confident that survival in the present trial is statistically different from that which established the SOC.

Previous studies have shown that survival can be positively correlated with the extent of the initial resection, which means that those patients having inoperable tumors have a lower probability of survival. The current trial incorporating TSC into the SOC RT and TMZ for GBM enrolled essentially equal numbers of patients who had undergone complete resection (14) and no resection (15). These patients comprised approximately 50% of the 59 patients enrolled in the trial. The other 50% were patients who had undergone partial resection.

It would be expected that the patients who have complete resections would have higher survivability rates than those solely having needle biopsies (i.e., partial resections). However, contrary to this expectation, survival at 2 years was quite similar for both groups in the present trial. In the subgroup of patients considered inoperable, the chance of survival at two years for those who received TSC was increased by over 100%, as 40% in the TSC group were alive at two years compared to less than 20 percent in the control. For comparison, survivability of the biopsy-only patients was observed to be 42.9% at two years. All groups of patients administered TSC in addition to SOC treatment showed better survival at 2 years than the overall survival rate seen with the historical controls.

Tumor Sizes

One particularly unexpected result of the present study was the effect that the treatment had on reduction in tumor sizes. In the trials, 56 patients received full-dose TSC therapy. Of those patients, 4 did not live long enough to have an MRI study after baseline, 1 patient was censored, and 14 patients underwent complete resections. Thus, 37 patients had either partial resection or no resection (biopsy only) and their tumors could be followed over time. The vast majority of these 37 patients showed reduction in tumor size, with almost 20% of the full-dose patients showing complete elimination of tumors, which emphasizes the beneficial use of TSC for this indication. This effect has not been documented in humans in the art.

Thus, it is shown that TSC is effective on glioblastoma multiforme tumors when given at a low dose (0.25 mg/kg) 45 minutes before radiation was administered.

It will be readily apparent to those skilled in the art that the numerous modifications and additions can be made to both the present compounds and compositions, and the related methods without departing from the disclosed methods and compositions.

What is claimed is:

1. A method of treating brain cancer in a human comprising
    a) administering to the human a bipolar trans carotenoid salt having the formula:

YZ-TCRO-ZY, where:
    Y=a cation which can be the same or different,
    Z=a polar group which can be the same or different and which is associated with the cation, and
    TCRO=a linear trans carotenoid skeleton with conjugated carbon-carbon double bonds and single bonds, and having pendant groups X, wherein the pendant groups X, which can be the same or different, are a linear or branched hydrocarbon group having 10 or less carbon atoms, or a halogen, and
    b) administering to the human radiation therapy and chemotherapy,
    wherein said bipolar trans carotenoid salt is administered at a time and at a dose causing increased partial pressure of oxygen in the tumor during administration of said radiation therapy and wherein said bipolar trans carotenoid salt is administered at a dose of 0.15-0.35 mg/kg 45-60 minutes prior to administration of said radiation therapy, and wherein said chemotherapy is administered with and after said radiation therapy.

2. A method as in claim 1, wherein the bipolar trans carotenoid salt is trans sodium crocetinate (TSC).

3. A method as in claim 1, wherein the bipolar trans carotenoid salt is trans sodium crocetinate (TSC) administered at a dose of 0.25 mg/kg.

4. A method as in claim 1, wherein said radiation therapy is external beam radiation therapy.

5. A method as in claim 1, wherein said radiation therapy is administered 5 times per week for 6 weeks.

6. A method as in claim 1, wherein said administering chemotherapy is administering temozolomide 7 times per week for 6 weeks.

7. A method as in claim 1, wherein said brain cancer is a glioblastoma multiforme.

8. A method of treating cancer in a human comprising
    a) administering to the human a bipolar trans carotenoid salt having the formula:

YZ-TCRO-ZY where:
    Y=a cation which can be the same or different,
    Z=a polar group which can be the same or different and which is associated with the cation, and
    TCRO=a linear trans carotenoid skeleton with conjugated carbon-carbon double bonds and single bonds, and having pendant groups X, wherein the pendant groups X, which can be the same or different, are a linear or branched hydrocarbon group having 10 or less carbon atoms, or a halogen, and
    b) administering chemotherapy to the human,
    wherein said bipolar trans carotenoid salt is administered at a time and at a dose causing increased partial pressure of oxygen in the tumor during administration of said chemotherapy and wherein said bipolar trans carotenoid salt is administered at a dose of 0.75-2.0 mg/kg.

9. A method as in claim 8, wherein the bipolar trans carotenoid salt is trans sodium crocetinate (TSC) administered at a dose of 0.75-2.0 mg/kg 1-2 hours prior to administration of said chemotherapy.

10. A method as in claim 8, wherein said cancer is a solid tumor.

11. A method as in claim 8, wherein the cancer is selected from the group consisting of squamous cell carcinomas, melanomas, lymphomas, sarcomas, sarcoids, osteosarcomas, skin cancer, breast cancer, head and neck cancer, gynecological cancer, urological and male genital cancer, bladder cancer, prostate cancer, bone cancer, cancers of the endocrine glands, cancers of the alimentary canal, cancers of the major digestive glands/organs, CNS cancer, and lung cancer.

12. A method as in claim 8, wherein the cancer is pancreatic cancer.

13. A method as in claim 8, wherein said chemotherapy is selected from the group consisting of alkylating agents, antimetabolites, antitumor antibiotics, topoisomerase inhibitors, and anti-microtubule agents.

14. A method as in claim 8, wherein said chemotherapy is one or more compounds selected from the group consisting of temozolomide, gemcitabine, 5-fluorouracil (5-FU), irinotecan, oxaliplatin, nab-paclitaxel (albumin-bound paclitaxel), capecitabine, cisplatin, erlotinib, paclitaxel, docetaxel, and irinotecan liposome.

15. A method as in claim 8, wherein said chemotherapy is one or more compounds selected from gemcitabine, irinotecan, and celecoxib.

16. A method as in claim 8, wherein said chemotherapy is one or both of gemcitabine and nab-paclitaxel.

17. A method as in claim 8, wherein said chemotherapy is gemcitabine.

18. A method as in claim 8, wherein administering said bipolar trans carotenoid salt is administering 1.5 mg/kg trans sodium crocetinate (TSC) 1-2 hours prior to administering said chemotherapy, and administering said chemotherapy is administering gemcitabine as an IV infusion once per week for 3 weeks followed by a week of rest.

19. A method as in claim 8, wherein administering said bipolar trans carotenoid salt is administering 1.5 mg/kg trans sodium crocetinate (TSC) 1-2 hours prior to administering said chemotherapy, and administering said chemotherapy is administering nab-paclitaxel as an IV infusion followed by gemcitabine as an IV infusion, once per week for 3 weeks followed by a week of rest.

20. A method as in claim 8, wherein the bipolar trans carotenoid salt is trans sodium crocetinate (TSC).

21. A method as in claim 1, wherein the bipolar trans carotenoid salt is trans sodium crocetinate (TSC) in the form of a lyophilized composition with a cyclodextrin.

22. A method as in claim 2, wherein the TSC is in the form of a composition with a cyclodextrin.

23. A method as in claim 22, wherein the cyclodextrin is gamma-cyclodextrin.

24. A method as in claim 23, wherein said brain cancer is a glioblastoma multiforme.

25. A method as in claim 24, wherein said radiation therapy is administered 5 times per week for 6 weeks.

26. A method as in claim 25, wherein TSC is administered 3 times per week for the 6 weeks.

27. A method as in claim 24, wherein said chemotherapy is temozolomide.

28. A method as in claim 27, wherein said temozolomide is administered 7 times per week for 6 weeks.

29. A method as in claim 7, wherein said glioblastoma multiforme is considered inoperable.

30. A method of treating a glioblastoma multiforme in a human, wherein said glioblastoma multiforme is considered inoperable and wherein the method comprises administering to the human trans sodium crocetinate, radiation therapy, and chemotherapy, wherein said trans sodium crocetinate is administered at a dose of 0.15-0.35 mg/kg prior to administration of said radiation therapy, said chemotherapy is administered after said radiation therapy, and said trans sodium crocetinate is administered at a dose of 0.75-2.0 mg/kg prior to administration of said chemotherapy.

31. A method as in claim 30, wherein said trans sodium crocetinate is administered 45-60 minutes prior to administration of said radiation therapy.

32. A method as in claim 30, wherein said trans sodium crocetinate is administered 1-2 hours prior to administration of said chemotherapy.

33. A method as in claim 31, wherein said trans sodium crocetinate is administered 1-2 hours prior to administration of said chemotherapy.

* * * * *